US006217883B1

(12) United States Patent
Allan et al.

(10) Patent No.: US 6,217,883 B1
(45) Date of Patent: Apr. 17, 2001

(54) PORCINE CIRCOVIRUS AND PARAVOVIRUS VACCINE

(75) Inventors: Gordon Moore Allan; Brian Martin Meehan, both of Belfast (GB); John Albert Ellis, Saskatchewan (CA); George Steven Krakowka, Columbus, OH (US); Jean-ChrJistophe Francis Audonnet, Lyons (FR)

(73) Assignees: Merial, Lyons (FR); The Queen's University of Belfast, Belfast (GB); University of Saskatchewan, Saskatoon (CA)

( * ) Notice: Subject to any disclaimer, the term of this patent is extended or adjusted under 35 U.S.C. 154(b) by 0 days.

(21) Appl. No.: 09/347,594

(22) Filed: Jul. 1, 1999

(30) Foreign Application Priority Data

Jul. 6, 1998 (FR) .................................................. 98 08777

(51) Int. Cl.[7] ........................... A61K 39/295; C12N 7/00
(52) U.S. Cl. ..................... 424/202.1; 424/201.1; 424/264.1; 424/257.1; 424/229.1; 424/220.1; 424/209.1; 424/199.1; 424/815; 514/44; 435/235.1; 435/810
(58) Field of Search ............... 424/202.1, 233.1, 424/205.1, 184.1, 264.1, 257.1, 229.1, 220.1, 209.1, 199.1, 815; 435/5, 235.1, 810

(56) References Cited

U.S. PATENT DOCUMENTS 5,498,413  3/1996  Casal Alvarez et al. .......... 424/233.1

FOREIGN PATENT DOCUMENTS

WO 98 03658  1/1998  (FR) .

OTHER PUBLICATIONS

Database WPI,Section Ch, Week 9529, Derwent Publications Ltd., London, GB; Class B04, An 95–222945 XP002099703 & SU 1 538 305 A (Veterinary Preparations Res Inst), Dec. 15, 1994.

B.M. Meehan et al.: "Characterization of Novel Circovirus DNAS Associated with Wasting Syndromes in Pigs", Journal of General Virology, vol. 79, No. 9, pp. 2171–2179, CP002099702. (1998).

Vannier, et al. Study of the Efficacy of an Inactivated Virus Vaccine against Porcine Parvovirus. 1986. Ann. Rech. Vet. vol. 17, No. 4, pp. 425–432.

Izumida, et al. Establishment of the Attenuated Strain of Porcine Parvovirus for the Live Vaccine and its Biological–Immunological Characteristics, 1986. Japanese Veterinary Science. vol.48, No. 2, pp. 293–303.

Ellis, et al. Coinfection by porcine circoviruses and porcine parvovirus in pigs with naturally acquired postweaning multisystemic wasting syndrome. 2000. Journal of Veterinary Diagnostic Investigation. vol. 12, No. 1, pp. 21–27.

*Primary Examiner*—Mary E. Mosher
*Assistant Examiner*—Shanon Foley
(74) *Attorney, Agent, or Firm*—Frommer Lawrence & Haug LLP; William S. Frommer; Thomas J. Kowalski

(57) ABSTRACT

The invention relates to antigenic preparations and vaccines directed against the porcine multisystemic wasting syndrome (PMWS), comprising at least one porcine circovirus antigen, preferably type II, and at least one porcine parvovirus antigen.

30 Claims, 12 Drawing Sheets

FIG. 1a

| FIG. 1 | FIG. 1a<br>FIG. 1b |
|---|---|

Sequence of the PCV Imp1011-48121 isolate (SEQ ID No. 1)

1 AATTCAACCT TAACCTTTCT TATTCTGTAG TATTCAAAGG GCACAGAGCG

51 GGGGTTTGAG CCCCCTCCTG GGGGAAGAAA GTCATTAATA TTGAATCTCA

101 TCATGTCCAC CGCCCAGGAG GGCGTTCTGA CTGTGGTTCG CTTGACAGTA

151 TATCCGAAGG TGCGGGAGAG GCGGGTGTTG AAGATGCCAT TTTTCCTTCT

201 CCAGCGGTAA CGGTGGCGGG GGTGGACGAG CCAGGGGCGG CGGCGGAGGA

251 TCTGGCCAAG ATGGCTGCGG GGGCGGTGTC TTCTTCTCCG GTAACGCCTC

301 CTTGGATACG TCATATCTGA AAACGAAAGA AGTGCGCTGT AAGTATTACC

351 AGCGCACTTC GGCAGCGGCA GCACCTCGGC AGCACCTCAG CAGCAACATG

401 CCGAGCAAGA AGAATGGAAG AAGCGGACCC CAACCCCATA AAAGGTGGGT

451 GTTCACTCTG AATAATCCTT CCGAAGACGA GCGCAAGAAA ATACGGGATC

501 TTCCAATATC CCTATTTGAT TATTTTATTG TTGGCGAGGA GGGTAATGAG

551 GAAGGACGAA CACCTCACCT CCAGGGGTTC GCTAATTTTG TGAAGAAGCA

601 GACTTTTAAT AAAGTGAAGT GGTATTTGGG TGCCCGCTGC CACATCGAGA

651 AAGCGAAAGG AACAGATCAG CAGAATAAAG AATACTGCAG TAAAGAAGGC

701 AACTTACTGA TGGAGTGTGG AGCTCCTAGA TCTCAGGGAC AACGGAGTGA

751 CCTGTCTACT GCTGTGAGTA CCTTGTTGGA GAGCGGGAGT CTGGTGACCG

801 TTGCAGAGCA GCACCCTGTA ACGTTTGTCA GAAATTTCCG CGGGCTGGCT

851 GAACTTTTGA AAGTGAGCGG GAAAATGCAG AAGCGTGATT GGAAGACTAA

901 TGTacACGTC ATTGTGGGGC CACCTGGGTG TGGTAAAAGC AAATGGGCTG

951 CTAATTTTGC AGACCCGGAA ACCACATACT GGAAACCACC TAGAAACAAG

1001 TGGTGGGATG GTTACCATGG TGAAGAAGTG GTTGTTATTG ATGACTTTTA

1051 TGGCTGGCTG CCCTGGGATG ATCTACTGAG ACTGTGTGAT CGATATCCAT

1101 TGACTGTAGA GACTAAAGGT GGAACTGTAC CTTTTTTGGC CCGCAGTATT

1151 CTGATTACCA GCAATCAGAC CCCGTTGGAA TGGTACTCCT CAACTGCTGT

1201 CCCAGCTGTA GAAGCTCTTT ATCGGAGGAT TACTTCCTTG GTATTTTGGA

FIG. 1b   FIG. 1 | FIG. 1a / FIG. 1b

```
1251   AGAATGCTAC AGAACAATCC ACGGAGGAAG GGGGCCAGTT CGTCACCCTT

1301   TCCCCCCGAT GCCCTGAATT TCCATATGAA ATAAATTACT GAGTCTTTTT

1351   TATCACTTCG TAATGGTTTT TATTATTCAT TAAGGGTTAA GTGGGGGGTC

1401   TTTAAGATTA AATTCTCTGA ATTGTACATA CATGGTTACA CGGATATTGT

1451   ATTCCTGGTC GTATATACTG TTTTCGAACG CAGTGCCGAG GCCTACGTGG

1501   TCtACATTTC CAGCAGTTTG TAGTCTCAGC CACAGCTGGT TTCTTTTGTT

1551   GTTTGGTTGG AAGTAATCAA TAGTGGAATC TAGGACAGGT TTGGGGGTAA

1601   AGTAGCGGGA GTGGTAGGAG AAGGGCTGGG TTATGGTATG GCGGGAGGAG

1651   TAGTTTACAT AGGGGTCATA GGTGAGGGCT GTGGCCTTTG TTACAAAGTT

1701   ATCATCTAGA ATAACAGCAC TGGAGCCCAC TCCCCTGTCA CCCTGGGTGA

1751   TCGGGAGCA GGGCCAG
```

FIG. 2a

Sequence of the PCV Imp1011-48285 isolate (SEQ ID No. 2)

```
   1  AATTCAACCT TAACCTTTCT TATTCTGTAG TATTCAAAGG GCACAGAGCG
  51  GGGGTTTGAG CCCCCTCCTG GGGGAAGAAA GTCATTAATA TTGAATCTCA
 101  TCATGTCCAC CGCCCAGGAG GGCGTTTTGA CTGTGGTTCG CTTGACAGTA
 151  TATCCGAAGG TGCGGGAGAG GCGGGTGTTG AAGATGCCAT TTTTCCTTCT
 201  CCAGCGGTAA CGGTGGCGGG GGTGGACGAG CCAGGGGCGG CGGCGGAGGA
 251  TCTGGCCAAG ATGGCTGCGG GGGCGGTGTC TTCTTCTCCG GTAACGCCTC
 301  CTTGGATACG TCATATCTGA AAACGAAAGA AGTGCGCTGT AAGTATTACC
 351  AGCGCACTTC GGCAGCGGCA GCACCTCGGC AGCACCTCAG CAGCAACATG
 401  CCCAGCAAGA AGAATGGAAG AAGCGGACCC CAACCCCATA AAAGGTGGGT
 451  GTTCACTCTG AATAATCCTT CCGAAGACGA GCGCAAGAAA ATACGGGATC
 501  TTCCAATATC CCTATTTGAT TATTTTATTG TTGGCGAGGA GGGTAATGAG
 551  GAAGGACGAA CACCTCACCT CCAGGGGTTC GCTAATTTTG TGAAGAAGCA
 601  GACTTTTAAT AAAGTGAAGT GGTATTTGGG TGCCCGCTGC CACATCGAGA
 651  AAGCGAAAGG AACAGATCAG CAGAATAAAG AATACTGCAG TAAAGAAGGC
 701  AACTTACTGA TGGAGTGTGG AGCTCCTAgA TCTCAgGGAC AACGGAGTGA
 751  CCTGTCTACT GCTGTGAGTA CCTTGTTGGA GAGCGGGAGT CTGGTGACCG
 801  TTGCAGAGCA GCACCCTGTA ACGTTTGTCA GAAATTTCCG CGGGCTGGCT
 851  GAACTTTTGA AAGTGAGCGG GAAAATGCAG AAGCGTGATT GGAAGACTAA
 901  TGTACACGTC ATTGTGGGGC CACCTGGGTG TGGTAAAAGC AAATGGGCTG
 951  CTAATTTTGC AGACCCGGAA ACCACATACT GGAAACCACC TAGAAACAAG
1001  TGGTGGGATG GTTACCATGG TGAAGAAGTG GTTGTTATTG ATGACTTTTA
1051  TGGCTGGCTG CCCTGGGATG ATCTACTGAG ACTGTGTGAT CGATATCCAT
1101  TGACTGTAGA GACTAAAGGT GGAACTGTAC CTTTTTTGGC CCGCAGTATT
1151  CTGATTACCA GCAATCAGAC CCCGTTGGAA TGGTACTCCT CAACTGCTGT
1201  CCCAGCTGTA GAAGCTCTTT ATCGGAGGAT TACTTCCTTG GTATTTTGGA
```

FIG. 2b   FIG. 2 | FIG. 2a / FIG. 2b

```
1251  AGAATGCTAC AGAACAATCC ACGGAGGAAG GGGGCCAGTT CGTCACCCTT

1301  TCCCCCCCAT GCCCTGAATT CCATATGAA ATAAATTACT GAGTCTTTTT

1351  TATCACTTCG TAATGGTTTT TATTATTCAT TAAGGGTTAA GTGGGGGGTC

1401  TTTAAGATTA AATTCTCTGA ATTGTACATA CATGGTTACA CGGATATTGT

1451  ATTCCTGGTC GTATATACTG TTTTCGAACG CAGTGCCGAG GCCTACGTGG

1501  TCTACATTTC CAGTAGTTTG TAGTCTCAGC CACAGCTGAT TTCTTTTGTT

1551  GTTTGGTTGG AAGTAATCAA TAGTGGAATC TAGGACAGGT TTGGGGGTAA

1601  AGTAGCGGGA GTGGTAGGAG AAGGGCTGGG TTATGGTATG GCGGGAgGAG

1651  TAGTTTACAT AGGGGTCATA GGTGAgGGCT GTGGCCTTTG TTACAAAGTT

1701  ATCATCTAGA ATAACAGCAC TGGAGCCCAC TCCCTGTCA CCCTGGGTGA

1751  TCGGGAGCA GGGCCAG
```

FIG. 3a

Sequence of the PCV Imp999 isolate (SEQ ID No. 3)

```
   1  AATTCAACCT TAACCTTTTT TATTCTGTAG TATTCAAAGG GTATAGAGAT
  51  TTTGTTGGTC CCCCCTCCCG GGGGAACAAA GTCGTCAATA TTAAATCTCA
 101  TCATGTCCAC CGCCCAGGAG GGCGTTCTGA CTGTGGTAGC CTTGACAGTA
 151  TATCCGAAGG TGCGGGAGAG GCGGGTGTTG AAGATGCCAT TTTTCCTTCT
 201  CCAACGGTAG CGGTGGCGGG GGTGGACGAG CCAGGGGCGG CGGCGGAGGA
 251  TCTGGCCAAG ATGGCTGCGG GGGCGGTGTC TTCTTCTGCG GTAACGCCTC
 301  CTTGGATACG TCATAGCTGA AAACGAAAGA AGTGCGCTGT AAGTATTACC
 351  AGCGCACTTC GGCAGCGGCA GCACCTCGGC AGCACCTCAG CAGCAACATG
 401  CCCAGCAAGA AGAATGGAAG AAGCGGACCC CAACCACATA AAAGGTGGGT
 451  GTTCACGCTG AATAATCCTT CCGAAGACGA GCGCAAGAAA ATACGGGAGC
 501  TCCCAATCTC CCTATTTGAT TATTTTATTG TTGGCGAGGA GGGTAATGAG
 551  GAAGGACGAA CACCTCACCT CCAGGGGTTC GCTAATTTTG TGAAGAAGCA
 601  AACTTTTAAT AAAGTGAAGT GGTATTTGGG TGCCCGCTGC CACATCGAGA
 651  AAGCCAAAGG AACTGATCAG CAGAATAAAG AATATTGCAG TAAAGAAGGC
 701  AACTTACTTA TTGAATGTGG AGCTCCTCGA TCTCAAGGAC AACGGAGTGA
 751  CCTGTCTACT GCTGTGAGTA CCTTGTTGGA GAGCGGGAGT CTGGTGACCG
 801  TTGCAGAGCA GCACCCTGTA ACGTTTGTCA GAAATTTCCG CGGGCTGGCT
 851  GAACTTTTGA AAGTGAGCGG GAAAATGCAG AAGCGTGATT GGAAGACCAA
 901  TGTACACGTC ATTGTGGGGC CACCTGGGTG TGGTAAAAGC AAATGGGCTG
 951  CTAATTTTGC AGACCCGGAA ACCACATACT GGAAACCACC TAGAAACAAG
1001  TGGTGGGATG GTTACCATGG TGAAgAAGTG GTTGTTATTG ATGACTTTTA
1051  TGGCTGGCTG CCGTGGGATG ATCTACTGAG ACTGTGTGAT CGATATCCAT
1101  TGACTGTAGA GACTAAAGGT GGAACTGTAC CTTTTTTGGC CCGCAGTATT
1151  CTGATTACCA GCAATCAGAC CCCGTTGGAA TGGTACTCCT CAACTGCTGT
1201  CCCAGCTGTA GAAGCTCTCT ATCGGAGGAT TACTTCCTTG GTATTTTGGA
```

FIG. 3b

| | | | | |
|---|---|---|---|---|
| 1251 | AGAATGCTAC | AGAACAATCC | ACGGAGGAAG | GGGGCCAGTT | CGTCACCCTT |
| 1301 | TCCCCCCCAT | GCCCTGAATT | TCCATATGAA | ATAAATTACT | GAGTCTTTTT |
| 1351 | TATCACTTCG | TAATGGTTTT | TATTATTCAT | TTAGGGTTTA | AGTGGGGGGT |
| 1401 | CTTTAAGATT | AAATTCTCTG | AATTGTACAT | ACATGGTTAC | ACGGATATTG |
| 1451 | TAGTCCTGGT | CGTATATACT | GTTTTCGAAC | GCAGTGCCGA | GGCCTACGTG |
| 1501 | GTCCACATTT | CTAGAGGTTT | GTAGCCTCAG | CCAAAGCTGA | TTCCTTTTGT |
| 1551 | TATTTGGTTG | GAAGTAATCA | ATAGTGGAGT | CAAGAACAGG | TTTGGGTGTG |
| 1601 | AAGTAACGGG | AGTGGTAGGA | GAAGGGTTGG | GGGATTGTAT | GGCGGGAGGA |
| 1651 | GTAGTTTACA | TATGGGTCAT | AGGTTAGGGC | TGTGGCCTTT | GTTACAAAGT |
| 1701 | TATCATCTAG | AATAACAGCA | GTGGAGCCCA | CTCCCTATC | ACCCTGGGTG |
| 1751 | ATGGGGAGC | AGGGCCAG | | | |

FIG. 4a

Sequence of the PCV Imp1010 isolate (SEQ ID No. 4)

```
   1  AATTCAACCT TAACCTTTCT TATTCTGTAG TATTCAAAGG GTATAGAGAT
  51  TTTGTTGGTC CCCCCTCCCG GGGGAACAAA GTCGTCAATT TTAAATCTCA
 101  TCATGTCCAC CGCCCAGGAG GGCGTTGTGA CTGTGGTACG CTTGACAGTA
 151  TATCCGAAGG TGCGGGAGAG GCGGGTGTTG AAGATGCCAT TTTTCCTTCT
 201  CCAACGGTAG CGGTGGCGGG GGTGGACGAG CCAGGGGCGG CGGCGGAGGA
 251  TCTGGCCAAG ATGGCTGCGG GGCGGTGTC TTCTTCTGCG GTAACGCCTC
 301  CTTGGATACG TCATAGCTGA AAACGAAAGA AGTGCGCTGT AAGTATTACC
 351  AGCGCACTTC GGCAGCGGCA GCACCTCGGC AGCACCTCAG CAGCAACATG
 401  CCCAGCAAGA AGAATGGAAG AAGCGGACCC CAACCACATA AAAGGTGGGT
 451  GTTCACGCTG AATAATCCTT CCGAAGACGA GCGCAAGAAA ATACGGGAGC
 501  TCCCAATCTC CCTATTTGAT TATTTTATTG TTGGCGAGGA GGGTAATGAG
 551  GAAGGACGAA CACCTCACCT CCAGGGGTTC GCTAATTTTG TGAAGAAGCA
 601  AACTTTTAAT AAAGTGAAGT GGTATTTGGG TGCCCGCTGC CACATCGAGA
 651  AAGCCAAAGG AACTGATCAG CAGAATAAAG AATATTGCAG TAAAGAAGGC
 701  AACTTACTTA TTGAATGTGG AGCTCCTCGA TCTCAAGGAC AACGGAGTGA
 751  CCTGTCTACT GCTGTGAGTA CCTTGTTGGA GAGCGGGAGT CTGGTGACCG
 801  TTGCAGAGCA GCACCCTGTA ACGTTTGTCA GAAATTTCCG CGGGCTGGCT
 851  GAACTTTTGA AGTGAGCGG GAAAATGCAG AAGCGTGATT GGAAGACCAA
 901  TGTACACGTC ATTGTGGGGC CACCTGGGTG TGGTAAAAGC AAATGGGCTG
 951  CTAATTTTGC AGACCCGGAA ACCACATACT GGAAACCACC TAGAAACAAG
1001  TGGTGGGATG GTTACCATGG TGAAGAAGTG GTTGTTATTG ATGACTTTTA
1051  TGGCTGGCTG CCGTGGGATG ATCTACTGAG ACTGTGTGAT CGATATCCAT
1101  TGACTGTAGA GACTAAAGGT GGAACTGTAC CTTTTTTGGC CCGCAGTATT
1151  CTGATTACCA GCAATCAGAC CCCGTTGGAA TGGTACTCCT CAACTGCTGT
1201  CCCAGCTGTA GAAGCTCTCT ATCGGAGGAT TACTTCCTTG GTATTTGGA
```

FIG. 4b

| FIG. 4 | FIG. 4a |
|        | FIG. 4b |

```
1251   AGAATGCTAC AGAACAATCC ACGGAGGAAG GGGGCCAGTT CGTCACCCTT

1301   TCCCCCCCAT GCCCTGAATT TCCATATGAA ATAAATTACT GAGTCTTTTT

1351   TATCACTTCG TAATGGTTTT TATTATTCAT TTAGGGTTTA AGTGGGGGT

1401   CTTTAAGATT AAATTCTCTG AATTGTACAT ACATGGTTAC ACGGATATTG

1451   TAGTCCTGGT CGTATTTACT GTTTCGAAC GCAGCGCCGA GGCCTACGTG

1501   GTCCACATTT CCAGAGGTTT GTAGTCTCAG CCAAAGCTGA TTCCTTTTGT

1551   TATTTGGTTG GAAGTAATCA ATAGTGGAGT CAAGAACAGG TTTGGGTGTG

1601   AAGTAACGGG AGTGGTAGGA GAAGGGTTGG GGGATTGTAT GGCGGGAGGA

1651   GTAGTTTACA TATGGGTCAT AGGTTAGGGC TGTGGCCTTT GTTACAAAGT

1701   TATCATCTAG AATAACAGCA GTGGAGCCCA CTCCCTATC ACCCTGGGTG

1751   ATGGGGGAGC AGGGCCAG
```

FIG. 5a

| FIG. 5 | FIG. 5a |
|        | FIG. 5b |
|        | FIG. 5c |
|        | FIG. 5d |

CLUSTAL W multiple sequence alignment

```
PCVPK-15     AATTCATATTTAGCCTTTCTAATACGGTAGTATTGGAAAGGTAGGGGTAGGGGTTGGTG
IMP999-ECO   AATTCAACCTTAACCTTTTTTATTCTGTAGTATTCAAAGGGTATAGAGATTTTGTTGGTC
IMP1010-ST   AATTCAACCTTAACCTTTCTTATTCTGTAGTATTCAAAGGGTATAGAGATTTTGTTGGTC
IMP1011-48   AATTCAACCTTAACCTTTCTTATTCTGTAGTATTCAAAGGGCACAGAGCGGGGTTTGAG
IMP1011-48   AATTCAACCTTAACCTTTCTTATTCTGTAGTATTCAAAGGGCACAGAGCGGGGTTTGAG
             ******  ***  *****  *  **  * ********  **  **  *     *** *

PCVPK-15     CCGCCTGAGGGGGGGAGGAACTGGCCGATGTTGAATTTGAGGTAGTTAACATTCCAAGAT
IMP999-ECO   CCCCCTCCCGGGGGAACAAAGTCGTCAATATTAAATCTCATCATGTCCACCGCCCAGGAG
IMP1010-ST   CCCCCTCCCGGGGGAACAAAGTCGTCAATTTTAAATCTCATCATGTCCACCGCCCAGGAG
IMP1011-48   CCCCCTCCTGGGGGAAGAAAGTCATTAATATTGAATCTCATCATGTCCACCGCCCAGGAG
IMP1011-48   CCCCCTCCTGGGGGAAGAAAGTCATTAATATTGAATCTCATCATGTCCACCGCCCAGGAG
             ** ***   *****  *  **  *       **  ** ***  *    **  **   *** **

PCVPK-15     GGC--TGCGAGTATCCTCCTTTT-ATGGTGAGTACAAATTCTGTAGAAAGGCGGGAATTG
IMP999-ECO   GGCGTTCTGACTGTGGTAGCCTTGACAGTATATCCGAAGGTGCGGGAGAGGCGGGTGTTG
IMP1010-ST   GGCGTTGTGACTGTGGTACGCTTGACAGTATATCCGAAGGTGCGGGAGAGGCGGGTGTTG
IMP1011-48   GGCGTTCTGACTGTGGTTCGCTTGACAGTATATCCGAAGGTGCGGGAGAGGCGGGTGTTG
IMP1011-48   GGCGTTTTGACTGTGGTTCGCTTGACAGTATATCCGAAGGTGCGGGAGAGGCGGGTGTTG
             ***   *  ** *  *     *  **   **  *  *  **        ** ****** ***

PCVPK-15     AAGATACCCGTCTTTCGGCGCCATCTGTAACGGTTTCTGAAGGCGGGGTGTGCCAAATAT
IMP999-ECO   AAGATGCCATTTTTCCTTCTCCAACGGTAGCGGTGGC-GGGGGTGGA-CGAGCCAGGGGC
IMP1010-ST   AAGATGCCATTTTTCCTTCTCCAACGGTAGCGGTGGC-GGGGGTGGA-CGAGCCAGGGGC
IMP1011-48   AAGATGCCATTTTTCCTTCTCCAGCGGTAACGGTGGC-GGGGGTGGA-CGAGCCAGGGGC
IMP1011-48   AAGATGCCATTTTTCCTTCTCCAGCGGTAACGGTGGC-GGGGGTGGA-CGAGCCAGGGGC
             *****  **   *    * ***  *  ***  * *** ****  *   *  * ****

PCVPK-15     GGTCTTCTCCGGAGGATGTTTCCAAGATGGCTGCGGGGGCGGGTCCTTCTTCTGCGGTAA
IMP999-ECO   GG----CGGCGGAGGATCTGGCCAAGATGGCTGCGGGGGCGGTGTCTTCTTCTGCGGTAA
IMP1010-ST   GG----CGGCGGAGGATCTGGCCAAGATGGCTGCGGGGGCGGTGTCTTCTTCTCCGGTAA
IMP1011-48   GG----CGGCGGAGGATCTGGCCAAGATGGCTGCGGGGGCGGTGTCTTCTTCTCCGGTAA
IMP1011-48   GG----CGGCGGAGGATCTGGCCAAGATGGCTGCGGGGGCGGTGTCTTCTTCTCCGGTAA
             **     * ******** *  ********************  ******* * ****** ******

PCVPK-15     CGCCTCCTTGGCCACGTCATCCTATAAAAGTGAAAGAAGTGCGCTGCTGTAGTATTACCA
IMP999-ECO   CGCCTCCTTGGATACGTCATAGC-TGAAAACGAAAGAAGTGCGCTGTA--AGTATTACCA
IMP1010-ST   CGCCTCCTTGGATACGTCATAGC-TGAAAACGAAAGAAGTGCGCTGTA--AGTATTACCA
IMP1011-48   CGCCTCCTTGGATACGTCATATC-TGAAAACGAAAGAAGTGCGCTGTA--AGTATTACCA
IMP1011-48   CGCCTCCTTGGATACGTCATATC-TGAAAACGAAAGAAGTGCGCTGTA--AGTATTACCA
             **********   ******    *  ***  ************** *          *********

PCVPK-15     GCGCACTTCGGCAGCGGCAGCACCTCGGCAGCG--TCAGTG--AAAATGCCAAGCAAGAA
IMP999-ECO   GCGCACTTCGGCAGCGGCAGCACCTCGGCAGCACCTCAGCAGCAACATGCCCAGCAAGAA
IMP1010-ST   GCGCACTTCGGCAGCGGCAGCACCTCGGCAGCACCTCAGCAGCAACATGCCCAGCAAGAA
IMP1011-48   GCGCACTTCGGCAGCGGCAGCACCTCGGCAGCACCTCAGCAGCAACATGCCGAGCAAGAA
IMP1011-48   GCGCACTTCGGCAGCGGCAGCACCTCGGCAGCACCTCAGCAGCAACATGCCCAGCAAGAA
             *****************************        ****  **  ** ***** ********
```

FIG. 5b

| FIG. 5 | FIG. 5a |
|        | FIG. 5b |
|        | FIG. 5c |
|        | FIG. 5d |

```
PCVPK-15     ---------AAGCGGCCCGCAACCCCATAAGAGGTGGGTGTTCACCCTTAATAATCCTTC
IMP999-ECO   GAATGGAAGAAGCGGACCCCAACCACATAAAAGGTGGGTGTTCACGCTGAATAATCCTTC
IMP1010-ST   GAATGGAAGAAGCGGACCCCAACCACATAAAAGGTGGGTGTTCACGCTGAATAATCCTTC
IMP1011-48   GAATGGAAGAAGCGGACCCCAACCCCATAAAAGGTGGGTGTTCACTCTGAATAATCCTTC
IMP1011-48   GAATGGAAGAAGCGGACCCCAACCCCATAAAAGGTGGGTGTTCACTCTGAATAATCCTTC
             ****** ** ***** ***** ************ ** **********

PCVPK-15     CGAGGAGGAGAAAAACAAAATACGGGAGCTTCCAATCTCCCTTTTTGATTATTTTGTTTG
IMP999-ECO   CGAAGACGAGCGCAAGAAAATACGGGAGCTCCCAATCTCCCTATTTGATTATTTTATTGT
IMP1010-ST   CGAAGACGAGCGCAAGAAAATACGGGAGCTCCCAATCTCCCTATTTGATTATTTTATTGT
IMP1011-48   CGAAGACGAGCGCAAGAAAATACGGGATCTTCCAATATCCCTATTTGATTATTTTATTGT
IMP1011-48   CGAAGACGAGCGCAAGAAAATACGGGATCTTCCAATATCCCTATTTGATTATTTTATTGT
             *** ** ***      ** ********** ** **** ***** ************ **

PCVPK-15     CGGAGAGGAAGGTTTGGAAGAGGGTAGAACTCCTCACCTCCAGGGGTTTGCGAATTTTGC
IMP999-ECO   TGGCGAGGAGGGTAATGAGGAAGGACGAACACCTCACCTCCAGGGGTTCGCTAATTTTGT
IMP1010-ST   TGGCGAGGAGGGTAATGAGGAAGGACGAACACCTCACCTCCAGGGGTTCGCTAATTTTGT
IMP1011-48   TGGCGAGGAGGGTAATGAGGAAGGACGAACACCTCACCTCCAGGGGTTCGCTAATTTTGT
IMP1011-48   TGGCGAGGAGGGTAATGAGGAAGGACGAACACCTCACCTCCAGGGGTTCGCTAATTTTGT
             ** ***** ***    ** ** **  **** ****************** ** *******

PCVPK-15     TAAGAAGCAGACTTTTAACAAGGTGAAGTGGTATTTTGGTGCCCGCTGCCACATCGAGAA
IMP999-ECO   GAAGAAGCAAACTTTTAATAAAGTGAAGTGGTATTTGGGTGCCCGCTGCCACATCGAGAA
IMP1010-ST   GAAGAAGCAAACTTTTAATAAAGTGAAGTGGTATTTGGGTGCCCGCTGCCACATCGAGAA
IMP1011-48   GAAGAAGCAGACTTTTAATAAAGTGAAGTGGTATTTGGGTGCCCGCTGCCACATCGAGAA
IMP1011-48   GAAGAAGCAGACTTTTAATAAAGTGAAGTGGTATTTGGGTGCCCGCTGCCACATCGAGAA
             ******* ******* ** ************** ****** *******************

PCVPK-15     AGCGAAAGGAACCGACCAGCAGAATAAAGAATACTGCAGTAAAGAAGGCCACATACTTAT
IMP999-ECO   AGCCAAAGGAACTGATCAGCAGAATAAAGAATATTGCAGTAAAGAAGGCAACTTACTTAT
IMP1010-ST   AGCCAAAGGAACTGATCAGCAGAATAAAGAATATTGCAGTAAAGAAGGCAACTTACTTAT
IMP1011-48   AGCGAAAGGAACAGATCAGCAGAATAAAGAATACTGCAGTAAAGAAGGCAACTTACTGAT
IMP1011-48   AGCGAAAGGAACAGATCAGCAGAATAAAGAATACTGCAGTAAAGAAGGCAACTTACTGAT
             *** ******** ** ***************** ************** ** **** **

PCVPK-15     CGAGTGTGGAGCTCCGCGGAACCAGGGGAAGCGCAGCGACCTGTCTACTGCTGTGAGTAC
IMP999-ECO   TGAATGTGGAGCTCCTCGATCTCAAGGACAACGGAGTGACCTGTCTACTGCTGTGAGTAC
IMP1010-ST   TGAATGTGGAGCTCCTCGATCTCAAGGACAACGGAGTGACCTGTCTACTGCTGTGAGTAC
IMP1011-48   GGAGTGTGGAGCTCCTAGATCTCAGGGACAACGGAGTGACCTGTCTACTGCTGTGAGTAC
IMP1011-48   GGAGTGTGGAGCTCCTAGATCTCAGGGACAACGGAGTGACCTGTCTACTGCTGTGAGTAC
             ** **********   *  ** **  * **  * ** ***********************

PCVPK-15     CCTTTTGGAGACGGGGTCTTTGGTGACTGTAGCCGAGCAGTTCCCTGTAACGTATGTGAG
IMP999-ECO   CTTGTTGGAGAGCGGGAGTCTGGTGACCGTTGCAGAGCAGCACCCTGTAACGTTTGTCAG
IMP1010-ST   CTTGTTGGAGAGCGGGAGTCTGGTGACCGTTGCAGAGCAGCACCCTGTAACGTTTGTCAG
IMP1011-48   CTTGTTGGAGAGCGGGAGTCTGGTGACCGTTGCAGAGCAGCACCCTGTAACGTTTGTCAG
IMP1011-48   CTTGTTGGAGAGCGGGAGTCTGGTGACCGTTGCAGAGCAGCACCCTGTAACGTTTGTCAG
             * * ******* ***  * * ******* ** ** ****** ********** *** **

PCVPK-15     AAATTCCGCGGGCTGGCTGAACTTTTGAAAGTGAGCGGGAAGATGCAGCAGCGTGATTG
IMP999-ECO   AAATTCCGCGGGCTGGCTGAACTTTTGAAAGTGAGCGGGAAATGCAGAAGCGTGATTG
IMP1010-ST   AAATTCCGCGGGCTGGCTGAACTTTTGAAAGTGAGCGGGAAATGCAGAAGCGTGATTG
IMP1011-48   AAATTCCGCGGGCTGGCTGAACTTTTGAAAGTGAGCGGGAAATGCAGAAGCGTGATTG
IMP1011-48   AAATTCCGCGGGCTGGCTGAACTTTTGAAAGTGAGCGGGAAATGCAGAAGCGTGATTG
             ***************************************** ****** *********
```

FIG. 5c

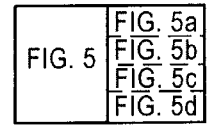

| | |
|---|---|
| PCVPK-15 | GAAGACAGCTGTACACGTCATAGTGGGCCCGCCCGGTTGTGGGAAGAGCCAGTGGGCCCG |
| IMP999-ECO | GAAGACCAATGTACACGTCATTGTGGGGCCACCTGGGTGTGGTAAAAGCAAATGGGCTGC |
| IMP1010-ST | GAAGACCAATGTACACGTCATTGTGGGGCCACCTGGGTGTGGTAAAAGCAAATGGGCTGC |
| IMP1011-48 | GAAGACTAATGTACACGTCATTGTGGGGCCACCTGGGTGTGGTAAAAGCAAATGGGCTGC |
| IMP1011-48 | GAAGACTAATGTACACGTCATTGTGGGGCCACCTGGGTGTGGTAAAAGCAAATGGGCTGC |
| | ****** ************* ***** ** ** ***** ** *** * ***** |
| PCVPK-15 | TAATTTTGCTGAGCCTAGGGACACCTACTGGAAGCCTAGTAGAAATAAGTGGTGGGATGG |
| IMP999-ECO | TAATTTTGCAGACCCGGAAACCACATACTGGAAACCACCTAGAAACAAGTGGTGGGATGG |
| IMP1010-ST | TAATTTTGCAGACCCGGAAACCACATACTGGAAACCACCTAGAAACAAGTGGTGGGATGG |
| IMP1011-48 | TAATTTTGCAGACCCGGAAACCACATACTGGAAACCACCTAGAAACAAGTGGTGGGATGG |
| IMP1011-48 | TAATTTTGCAGACCCGGAAACCACATACTGGAAACCACCTAGAAACAAGTGGTGGGATGG |
| | ********* ** ** *** ******* ** ****** ************* |
| PCVPK-15 | ATATCATGGAGAAGAAGTTGTTGTTTTGGATGATTTTTATGGCTGGTTACCTTGGGATGA |
| IMP999-ECO | TTACCATGGTGAAGAAGTGGTTGTTATTGATGACTTTTATGGCTGGCTGCCGTGGGATGA |
| IMP1010-ST | TTACCATGGTGAAGAAGTGGTTGTTATTGATGACTTTTATGGCTGGCTGCCGTGGGATGA |
| IMP1011-48 | TTACCATGGTGAAGAAGTGGTTGTTATTGATGACTTTTATGGCTGGCTGCCCTGGGATGA |
| IMP1011-48 | TTACCATGGTGAAGAAGTGGTTGTTATTGATGACTTTTATGGCTGGCTGCCCTGGGATGA |
| | ** ***** ******** ****** * ***** ************ * ** ******** |
| PCVPK-15 | TCTACTGAGACTGTGTGACCGGTATCCATTGACTGTAGAGACTAAAGGGGGTACTGTTCC |
| IMP999-ECO | TCTACTGAGACTGTGTGATCGATATCCATTGACTGTAGAGACTAAAGGTGGAACTGTACC |
| IMP1010-ST | TCTACTGAGACTGTGTGATCGATATCCATTGACTGTAGAGACTAAAGGTGGAACTGTACC |
| IMP1011-48 | TCTACTGAGACTGTGTGATCGATATCCATTGACTGTAGAGACTAAAGGTGGAACTGTACC |
| IMP1011-48 | TCTACTGAGACTGTGTGATCGATATCCATTGACTGTAGAGACTAAAGGTGGAACTGTACC |
| | ************** ** ***************************** ** ***** ** |
| PCVPK-15 | TTTTTTGGCCCGCAGTATTTTGATTACCAGCAATCAGGCCCCCCAGGAATGGTACTCCTC |
| IMP999-ECO | TTTTTTGGCCCGCAGTATTCTGATTACCAGCAATCAGACCCCGTTGGAATGGTACTCCTC |
| IMP1010-ST | TTTTTTGGCCCGCAGTATTCTGATTACCAGCAATCAGACCCCGTTGGAATGGTACTCCTC |
| IMP1011-48 | TTTTTTGGCCCGCAGTATTCTGATTACCAGCAATCAGACCCCGTTGGAATGGTACTCCTC |
| IMP1011-48 | TTTTTTGGCCCGCAGTATTCTGATTACCAGCAATCAGACCCCGTTGGAATGGTACTCCTC |
| | ***************** **************** ** * ************** |
| PCVPK-15 | AACTGCTGTCCCAGCTGTAGAAGCTCTCTATCGGAGGATTACTACTTTGCAATTTTGGAA |
| IMP999-ECO | AACTGCTGTCCCAGCTGTAGAAGCTCTCTATCGGAGGATTACTTCCTTGGTATTTTGGAA |
| IMP1010-ST | AACTGCTGTCCCAGCTGTAGAAGCTCTCTATCGGAGGATTACTTCCTTGGTATTTTGGAA |
| IMP1011-48 | AACTGCTGTCCCAGCTGTAGAAGCTCTTTATCGGAGGATTACTTCCTTGGTATTTTGGAA |
| IMP1011-48 | AACTGCTGTCCCAGCTGTAGAAGCTCTTTATCGGAGGATTACTTCCTTGGTATTTTGGAA |
| | *************************** *************** * *** ******** |
| PCVPK-15 | GACTGCTGGAGAACAATCCACGGAGGTACCCGAAGGCCGATTTGAAGCAGTGGACCCACC |
| IMP999-ECO | GAATGCTACAGAACAATCCACGGAGGAA---GGGGGCCAGTTCGTCACCCTTTCCCCCCC |
| IMP1010-ST | GAATGCTACAGAACAATCCACGGAGGAA---GGGGGCCAGTTCGTCACCCTTTCCCCCCC |
| IMP1011-48 | GAATGCTACAGAACAATCCACGGAGGAA---GGGGGCCAGTTCGTCACCCTTTCCCCCCC |
| IMP1011-48 | GAATGCTACAGAACAATCCACGGAGGAA---GGGGGCCAGTTCGTCACCCTTTCCCCCCC |
| | ** **** **************** * * **** ** * * * *** ** |
| PCVPK-15 | CTGTGCCCTTTTCCCATATAAAATAAATTACTGAGTCTTTTTTGTTATCACATCGTAATG |
| IMP999-ECO | ATGCCCTGAATTTCCATATGAAATAAATTACTGAGTCTTTTT---TATCACTTCGTAATG |
| IMP1010-ST | ATGCCCTGAATTTCCATATGAAATAAATTACTGAGTCTTTTT---TATCACTTCGTAATG |
| IMP1011-48 | ATGCCCTGAATTTCCATATGAAATAAATTACTGAGTCTTTTT---TATCACTTCGTAATG |
| IMP1011-48 | ATGCCCTGAATTTCCATATGAAATAAATTACTGAGTCTTTTT---TATCACTTCGTAATG |
| | ** * ** ****** ******************** ****** ******** |

FIG. 5d

FIG. 5 | FIG. 5a
       | FIG. 5b
       | FIG. 5c
       | FIG. 5d

```
PCVPK-15      GTTTTTATT-TTTATTTA---TTTA----GAGGGTCTTTTAGGATAAATTCTCTGAATTG
IMP999-ECO    GTTTTTATTATTCATTTAGGGTTTAAGTGGGGGGTCTTTAAGATTAAATTCTCTGAATTG
IMP1010-ST    GTTTTTATTATTCATTTAGGGTTTAAGTGGGGGGTCTTTAAGATTAAATTCTCTGAATTG
IMP1011-48    GTTTTTATTATTCATTAAGGGTT-AAGTGGGGGGTCTTTAAGATTAAATTCTCTGAATTG
IMP1011-48    GTTTTTATTATTCATTAAGGGTT-AAGTGGGGGGTCTTTAAGATTAAATTCTCTGAATTG
              ********* ** *** *   ** *   * ******* ** ****************

PCVPK-15      TACATAAATAGTCAGCCTTACCACATAATTTTGGGCTGTGGCTGC-ATTTTGGAGCGCAT
IMP999-ECO    TACATACATGGTTACACGGATATTGTAGTCCTGG-TCGTATATACTGTTTTCGAACGCAG
IMP1010-ST    TACATACATGGTTACACGGATATTGTAGTCCTGG-TCGTATTTACTGTTTTCGAACGCAG
IMP1011-48    TACATACATGGTTACACGGATATTGTATTCCTGG-TCGTATATACTGTTTTCGAACGCAG
IMP1011-48    TACATACATGGTTACACGGATATTGTATTCCTGG-TCGTATATACTGTTTTCGAACGCAG
              ****** ** ** * *    ** * ***   **   *  * **** ** ****

PCVPK-15      AGCCGAGGCCTGTGTGCTCGACATTGGTGTGGGTATTTAAATGGAGCCACAGCTGGTTTC
IMP999-ECO    TGCCGAGGCCTACGTGGTCCACATTTCTAGAGGTTTGTAGCCTCAGCCAAAGCTGATTCC
IMP1010-ST    CGCCGAGGCCTACGTGGTCCACATTTCCAGAGGTTTGTAGTCTCAGCCAAAGCTGATTCC
IMP1011-48    TGCCGAGGCCTACGTGGTCTACATTTCCAGCAGTTTGTAGTCTCAGCCACAGCTGGTTTC
IMP1011-48    TGCCGAGGCCTACGTGGTCTACATTTCCAGTAGTTTGTAGTCTCAGCCACAGCTGATTTC
              ********** *** ** *****   **  **  ** * **  ***** ***** **  *

PCVPK-15      TTTTATTATTTGGGTGGAACCAATCAATTGTTTGGTCCAGCTCAGGTTTGGGGGTGAAGT
IMP999-ECO    TTTTGTTATTTGGTTGGAAGTAATCAATAGTGGAGTCAAGAACAGGTTTGGGTGTGAAGT
IMP1010-ST    TTTTGTTATTTGGTTGGAAGTAATCAATAGTGGAGTCAAGAACAGGTTTGGGTGTGAAGT
IMP1011-48    TTTTGTTGTTTGGTTGGAAGTAATCAATAGTGGAATCTAGGACAGGTTTGGGGGTAAAGT
IMP1011-48    TTTTGTTGTTTGGTTGGAAGTAATCAATAGTGGAATCTAGGACAGGTTTGGGGGTAAAGT
              **** ** ***** ***** *******  **  ** **  ********** ** ****

PCVPK-15      ACCTGGAGTGGTAGGTAAAGGGCTGCCTTATGGTGTGGCGGGAGGAGTAGTTAATATAGG
IMP999-ECO    AACGGGAGTGGTAGGAGAAGGGTTGGGGGATTGTATGGCGGGAGGAGTAGTTTACATATG
IMP1010-ST    AACGGGAGTGGTAGGAGAAGGGTTGGGGGATTGTATGGCGGGAGGAGTAGTTTACATATG
IMP1011-48    AGCGGGAGTGGTAGGAGAAGGGCTGGGTTATGGTATGGCGGGAGGAGTAGTTTACATAGG
IMP1011-48    AGCGGGAGTGGTAGGAGAAGGGCTGGGTTATGGTATGGCGGGAGGAGTAGTTTACATAGG
              * * ********** ***** **   ** **  ****************  * *** *

PCVPK-15      GGTCATAGGCCAAGTTGGTGGAGGGGGTTACAAAGTTGGCATCCAAGATAACAACAGTGG
IMP999-ECO    GGTCATAGGTTAGGGCTGTGGCCTTTGTTACAAAGTTATCATCTAGAATAACAGCAGTGG
IMP1010-ST    GGTCATAGGTTAGGGCTGTGGCCTTTGTTACAAAGTTATCATCTAGAATAACAGCAGTGG
IMP1011-48    GGTCATAGGTGAGGGCTGTGGCCTTTGTTACAAAGTTATCATCTAGAATAACAGCACTGG
IMP1011-48    GGTCATAGGTGAGGGCTGTGGCCTTTGTTACAAAGTTATCATCTAGAATAACAGCACTGG
              *********  *  * **  ****  ** ***** **** *  ****** ** ***

PCVPK-15      ACCCAACACCTCTTTGATTAGAGGTGATGGGGTCTCTGGGGTAA
IMP999-ECO    AGCCCACTCCCCTATCACCCTGGGTGATGGGGGAGCAGGGCCAG
IMP1010-ST    AGCCCACTCCCCTATCACCCTGGGTGATGGGGGAGCAGGGCCAG
IMP1011-48    AGCCCACTCCCCTGTCACCCTGGGTGATCGGGGAGCAGGGCCAG
IMP1011-48    AGCCCACTCCCCTGTCACCCTGGGTGATCGGGGAGCAGGGCCAG
              * ** ** ** ** * *    ****** ***  *   ***  *
```

PORCINE CIRCOVIRUS AND PARAVOVIRUS VACCINE

This application claims priority from French application No. 98 08777, filed Jul. 6, 1998. Reference is also made to U.S. application Ser. No. 09/161,092, filed Sep. 25, 1998 as a continuation-in-part of U.S. application Ser. No. 09/082,558, filed May 21, 1998, claiming priority from French applications Nos. 97 12382, 98 00873 and 98 03707, filed Oct. 3, 1997, Jan. 22, 1998 and Mar. 20, 1998, respectively. Reference is further made to the U.S. applications of Audonnet et al. and Bublot et al., Ser. Nos. 60/138,352 and 60/138,478, respectively, both filed Jun. 10, 1999 ("DNA VACCINE-PCV", and "PORCINE CIRCOVIRUS RECOMBINANT POXVIRUS VACCINE", respectively; attorney dockets 454313-2335 and TH-015, respectively). Reference is additionally made to each of the documents cited in the text and in the record or prosecution of each of the aforementioned U.S. and French applications, including without limitation WO 98/03658, published Jan. 29, 1998 from PCT/FR97/01313, filed Jul. 15, 1997 and designating the U.S. and claiming priority from French application 96 09338, filed Jul. 19, 1996 (the U.S. continuation-in-part of PCT/FR97/01313 being U.S. application Ser. No. 09/232,468, filed Jan. 15, 1999). Each of the aforementioned U.S., PCT and French applications (including parenthetically), and each document cited in the text and the record or prosecution of each of the aforementioned U.S., PCT and French applications (including parenthetically), is hereby incorporated herein by reference; and, technology in each of the aforementioned U.S., PCT and French applications (including parenthetically), and each document cited in the text and the record or prosecution of each of the aforementioned U.S., PCT and French applications (including parenthetically) can be used in the practice of this invention.

Furthermore, with respect to equivalent sequences capable of hybridizing under high stringency conditions or having a high homology with nucleic acid molecules employed in the invention, "hybridizing under high stringency conditions" can be synonymous with "stringent hybridization conditions", a term which is well known in the art; see, for example, Sambrook, "Molecular Cloning, A Laboratory Manual" second ed., CSH Press, Cold Spring Harbor, 1989; "Nucleic Acid Hybridisation, A Practical Approach", Hames and Higgins eds., IRL Press, Oxford, 1985; both incorporated herein by reference. With respect to nucleic acid molecules and polypeptides which can be used in the practice of the invention, the nucleic acid molecules and polypeptides advantageously have at least about 84 to 85% or greater homology or identity, such as at least about 85% or about 86% or about 87% or about 88% or about 89% homology or identity, for instance at least about 90% or homology or identity or greater, such as at least about 91%, or about 92%, or about 93%, or about 94% identity or homology, more advantageously at least about 95% to 99% homology or identity or greater, such as at least about 95% homology or identity or greater e.g., at least about 96%, or about 97%, or about 98%, or about 99%, or even about 100% identity or homology, or from about 84 to about 100% or from about 90 to about 99 or about 100% or from about 95 to about 99 or about 100% identity or homology, with respect to sequences disclosed or described herein and fragments thereof herein disclosed or described (including subsequences discussed below); and thus, the invention comprehends a vector encoding an epitope or epitopic region of a PCV isolate or a composition comprising such an epitope, compositions comprising an epitope or epitopic region of a PCV isolate, and methods for making and using such vectors and compositions, e.g., the invention also comprehends that these nucleic acid molecules and polypeptides can be used in the same fashion as the herein mentioned nucleic acid molecules, fragments thereof and polypeptides. In this regard, it is noted that homology between PCV1 and PCV2 is about 84% to about 85% and that within the PCV2 group homology is from about 95% to about 99%.

Nucleotide sequence homology can be determined using the "Align" program of Myers and Miller, ("Optimal Alignments in Linear Space", CABIOS 4, 11–17, 1988, incorporated herein by reference) and available at NCBI. Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})* 100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman, 1983 PNAS USA 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. Calif.). When RNA sequences are said to be similar, or have a degree of sequence identity or homology with DNA sequences, thymidine (T) in the DNA sequence is considered equal to uracil (U) in the RNA sequence (see also alignment used in Figures and in Appendix I). RNA sequences within the scope of the invention can be derived from DNA sequences, by thymidine (T) in the DNA sequence being considered equal to uracil (U) in RNA sequences.

Additionally or alternatively, amino acid sequence similarity or identity or homology can be determined using the BlastP program (Altschul et al., Nucl. Acids Res. 25, 3389–3402, incorporated herein by reference) and available at NCBI (used in determining sequence homology, as shown in Appendix I; see also the Examples). The following references (each incorporated herein by reference) also provide algorithms for comparing the relative identity or homology of amino acid residues of two proteins, and additionally or alternatively with respect to the foregoing, the teachings in these references can be used for determining percent homology or identity: Needleman S B and Wunsch C D, "A general method applicable to the search for similarities in the amino acid sequences of two proteins," *J. Mol. Biol.* 48:444–453 (1970); Smith T F and Waterman M S, "Comparison of Bio-sequences," *Advances in Applied Mathematics* 2:482–489 (1981); Smith T F, Waterman M S and Sadler J R, "Statistical characterization of nucleic acid sequence functional domains," *Nucleic Acids Res.,* 11:2205–2220 (1983); Feng D F and Dolittle R F, "Progressive sequence alignment as a prerequisite to correct phylogenetic trees," *J. of Molec. Evol.,* 25:351–360 (1987); Higgins D G and Sharp P M, "Fast and sensitive multiple sequence alignment on a microcomputer," *CABIOS*, 5:151–153 (1989); Thompson J D, Higgins D G and Gibson T J, "ClusterW: improving the sensitivity of progressive multiple sequence alignment through sequence weighing, positions-specific gap penalties and weight matrix choice, *Nucleic Acid Res.*, 22:4673–480 (1994); and, Devereux J, Haeberlie P and Smithies O, "A comprehensive set of sequence analysis program for the VAX," *Nucl. Acids Res.*, 12: 387–395 (1984).

The disclosed nucleic acid sequences or portions or fragments thereof, e.g., subsequences comprising at least about 12 nucleotides in length, for instance, at least about 15, about 18, about 21, about 24 or about 27 nucleotides in length, such as at least about 30, about 33, about 36, about 39 or about 42 nucleotides in length, for example, a nucleic acid molecule of at least about 12 nucleotides in length such as about 12 to about 30, about 12 to about 50 or about 12 to about 60, or about 12 to about 75 or about 12 to about 100 or more nucleotides in length may be useful in hybridization, e.g., as probes or primers; and, the invention further comprehends vectors or plasmids containing and/or expressing such a nucleic acid molecule, as such as a nucleic acid molecule can encode an epitope or an epitopic region or a polypeptide which is functionally equivalent to polypeptides expressed by herein mentioned sequences, well as uses of such nucleic acid molecules, e.g., for expression thereof either in vitro or in vivo, or for amplifying or detecting a herein defined gene or a homolog thereof, and the use of such vectors, e.g., in inventive compositions.

The nucleic acids used for hybridization can, of course, be conveniently labeled by incorporating or attaching, e.g., a radioactive or other marker. Such markers are well known in the art. The labeling of said nucleic acid molecules can be effected by conventional methods. The presence or expression of PCV or genes thereof can be monitored by using a primer pair that specifically hybridizes to either of the corresponding nucleic acid sequences and by carrying out a PCR reaction according to standard procedures. Specific hybridization of the above mentioned probes or primers preferably occurs at stringent hybridization conditions. A probe or primer can be any stretch of at least 8, preferably at least 10, more preferably at least 12, 13, 14, or 15, such as at least 20, e.g., at least 23 or 25, for instance at least 27 or 30 nucleotides in a herein defined nucleic acid molecule which are unique thereto; and, advantageously the probe or primer encodes an epitope or epitopic region, such that the probe or primer can also be useful for expression of an antigenic or immunogenic polypeptide whereby the polypeptide or a vector expressing it are useful in inventive compositions. As to PCR or hybridization primers or probes and optimal lengths therefor, reference is also made to Kajimura et al., GATA 7(4):71–79 (1990), incorporated herein by reference. Furthermore, expression of PCV nucleic acid molecules are useful in generating antibodies, which antibodies can be used to detect the presence or absence of PCV (or antigens thereof) in a sample or specimen; or, the expressed polypeptides can be used to detect the presence or absence of antibodies to PCV in a sample or specimen. Thus, nucleic acid molecules and expression products thereof have diagnostic utilities too.

The invention is discussed in more detail in the following text.

The present invention relates to a vaccine against the PMWS syndrome (Porcine Multisystemic Wasting Syndrome also called Post-Weaning Multisystemic Wasting Syndrome).

Various documents are cited in the following text, and various documents are referenced or cited in documents cited in the following text. There is no admission that any of these documents are indeed prior art as to the present invention. All documents cited herein and all documents referenced or cited in documents cited herein are hereby incorporated herein by reference.

PCV (for "Porcine CircoVirus") was originally detected as a noncytopathogenic contaminant in pig kidney cell lines PK/15. This virus was classified among the Circoviridae with the chicken anaemia virus (CAV for Chicken Anaemia Virus) and the PBFDV virus (Pscittacine Beak and Feather Disease Virus). It is a small nonenveloped virus (from 15 to 24 nm) whose common characteristic is to contain a genome in the form of a circular single-stranded DNA of 1.76 to 2.31 kb. It was first thought that this genome encoded a polypeptide of about 30 kDa (Todd et al., Arch Virol 1991, 117; 129–135). Recent work has however shown a more complex transcription (Meehan B. M. et al., 1997, 78; 221–227). Moreover, no significant homologies in nucleotide sequence or in common antigenic determinants are known between the three types of circoviruses known.

The PCV derived from the PK/15 cells is considered not to be pathogenic. Its sequence is known from B. M. Meehan et al., J. Gen. Virol 1997 (78) 221–227. It is only very recently that some authors have thought that strains of PCV could be pathogenic and associated with the PMWS syndrome (Gupi P. S. Nayar et al., Can. Vet. J, vol. 38, 1997: 385–387 and Clark E. G., Proc. Am. Assoc. Swine Prac. 1997; 499–501). Nayar et al. have detected PCV DNA in pigs having the PMWS syndrome using PCR techniques.

The PMWS syndrome detected in Canada, the United States and France is clinically characterized by a gradual loss of weight and by manifestations such as tachypnea, dyspnea and jaundice. From the pathological point of view, it is manifested by lymphocytic or granulomatous infiltrations, lymphadenopathies and, more rarely, by hepatitis and lymphocytic or granulomatous nephritis (Clark E. G., Proc. Am. Assoc. Swine Prac. 1997; 499–501; La Semaine Vétérinaire No. 26, supplement to La Semaine Vétérinaire 1996 (834); La Semaine Vétérinaire 1997 (857): 54; Gupi P. S. Nayar et al., Can. Vet. J, vol. 38, 1997; 385–387).

The applicant has succeeded in isolating five new PCV strains from pulmonary or ganglionic samples obtained from farms situated in Canada, the United States (California) and France (Brittany). These viruses have been detected in lesions in pigs with the PMWS syndrome, but not in healthy pigs.

The applicant has, in addition, sequenced the genome of four of these strains, namely the strains obtained from Canada and the United States as well as two French strains. The strains exhibit a very strong homology with each other at the nucleotide level, exceeding 96% and much weaker with the PK/15 strain, about 76%. The new strains can thus be considered as being representative of a new type of porcine circovirus, called here type II, type I being represented by PK/15.

Purified preparations of five strains were deposited under the Budapest Treaty at the ECACC (European Collection of Cell Cultures, Centre for Applied Microbiology & Research, Porton Down, Salisbury, Wiltshire SP4 OJG, United Kingdom) on Thursday Oct. 2, 1997:

accession No. V97100219 (called here Imp. 1008PCV)
    accession No. V97100218 (called here Imp. 1010PCV)
    accession No. V97100217 (called here Imp. 999PCV),
        and, on Friday Jan. 16, 1998:

accession No. V98011608 (called here Imp. 1011-48285) accession No. V98011609 (called here Imp. 1011-48121).

The applicant has observed that, in a trial for experimental reproduction of the porcine multisystemic wasting syndrome, a porcine parvovirus combined with the porcine circovirus could lead to a worsening of the disease.

The subject of the present invention is therefore a vaccination of pigs using a porcine circovirus, in particular type I or type II, preferably type II, vaccine, combined with a vaccination with a porcine parvovirus vaccine. This is understood to mean vaccination with either a bivalent vaccine, or the simultaneous use, in pigs, of a porcine circovirus vaccine and of a porcine parvovirus vaccine.

The reference parvovirus strain is the NADL-2 strain which is accessible from the ATCC collection under the reference VR-742. Vaccination against the porcine parvovirus is well known to persons skilled in the art and vaccines against the porcine parvovirus are commercially available. There may be mentioned by way of example: Parvovax® (inactivated vaccine against porcine parvovirosis, distributed by MERIAL). See also e.g. P. Vannier et A. Laval., Point. Vét. 1993, 25 (151),53–60 ; G. Florent et al., Proceedings of the Ninth Congress of Pig Veterinary Society, July 15–18, 1986, Barcelona, Spain. For DNA vaccines, one can refer e.g. to WO-A-98 03658.

The subject of the present invention is therefore an antigenic preparation directed against the PMWS syndrome, comprising at least one porcine circovirus antigen (preferably type II circovirus) and at least one porcine parvovirus antigen. In accordance with the invention, the porcine circovirus antigen (preferably type II circovirus) and the porcine parvovirus antigen comprise, independently of each other, an antigen chosen from the group consisting of an attenuated live whole antigen, an inactivated whole antigen, a subunit antigen, a recombinant live vector and a DNA vector. It is understood that the combination according to the invention may involve the use of any appropriate antigen or antigenic preparation form, it being understood that it is not necessary to use the same form for a given combination. The antigenic preparation may comprise, in addition, as is known per se, a vehicle or excipient acceptable from the veterinary point of view, and optionally an adjuvant acceptable from the veterinary point of view.

The subject of the present invention is also an immunogenic composition or a vaccine against the PMWS syndrome, comprising an effective quantity of circovirus+ parvovirus antigenic preparation as described above, in a vehicle or excipient acceptable from the veterinary point of view, and optionally an adjuvant acceptable from the veterinary point of view. An immunogenic composition elicits an immunological response which can, but need not be, protective. A vaccine composition elicits a protective response. Accordingly, the term "immunogenic composition" include a vaccine composition (as the former term can be protective composition).

The subject of the invention is also an immunological or a vaccination kit containing, packaged separately, an antigenic preparation or an immunogenic composition or a vaccine against the porcine circovirus and an antigenic preparation or an immunogenic composition or a vaccine against the porcine parvovirus. This kit may have the various characteristics set out above for the antigenic preparations, immunogenic compositions and vaccines.

The subject of the invention is also a method of immunization or of vaccination against the PMWS syndrome, comprising the administration of an immunogenic composition or a vaccine against the porcine circovirus and of an immunogenic composition or a vaccine against the porcine parvovirus or the administration of a bivalent immunogenic composition or vaccine, comprising, in the same formulation, an antigenic preparation specific to each virus. This method of immunisation or vaccination uses in particular the vaccines as defined above.

The subject of the invention is also the use of an antigenic preparation or of an immunogenic composition or a vaccine against the parvovirus, as in particular defined supra, for the preparation of a pharmaceutical composition intended to be used in the context of the prevention of the PMWS syndrome, in combination with an antigenic preparation or an immunogenic composition or a vaccine against the porcine circovirus.

For the production of circovirus antigenic preparations, the circoviruses may be obtained after passage on cells, in particular cell lines, e.g. PK/15 cells. The culture supernatants or extracts, optionally purified by standard techniques, may be used as antigenic preparation.

In the context of attenuated antigenic preparations and attenuated immunogenic compositions or vaccines, the attenuation may be carried out according to the customary methods, e.g. by passage on cells, preferably by passage on pig cells, especially cell lines, such as PK/15 cells (for example from 50 to 150, especially of the order of 100, passages). These immunogenic compositions and vaccines comprise in general a vehicle or diluent acceptable from the veterinary point of view, optionally an adjuvant acceptable from the veterinary point of view, as well as optionally a freeze-drying stabilizer.

These antigenic preparations, immunogenic compositions and vaccines will preferably comprise from $10^3$ to $10^7$ TCID50 of the attenuated virus in question.

They may be antigenic preparations, immunogenic compositions and vaccines based on inactivated whole antigen. The inactivated immunogenic compositions and vaccines comprise, in addition, a vehicle or a diluent acceptable from the veterinary point of view, with optionally in addition an adjuvant acceptable from the veterinary point of view.

The circoviruses according to the invention, with the fractions which may be present, are inactivated according to techniques known to persons skilled in the art. The inactivation will be preferably carried out by the chemical route, e.g. by exposing the antigen to a chemical agent such as formaldehyde (formalin), paraformaldehyde, β-propiolactone or ethyleneimine or its derivatives. The preferred method of inactivation will be herein the exposure to a chemical agent and in particular to ethyleneimine or to β-propiolactone.

Preferably, the inactivated antigenic preparations and the inactivated immunogenic compositions and vaccines according to the invention will be supplemented with adjuvant, advantageously by being provided in the form of emulsions, for example water-in-oil or oil-in-water, according to techniques well known to persons skilled in the art. It will be possible for the adjuvant character to also come from the incorporation of a customary adjuvant compound into the active ingredient.

Among the adjuvants which may be used, there may be mentioned by way of example aluminium hydroxide, the saponines (e.g. Quillaja saponin or Quil A; see Vaccine Design, The Subunit and Adjuvant Approach, 1995, edited by Michael F. Powel and Mark J. Newman, Plennum Press, New-York and London, p.210), Avridine® (Vaccine Design p. 148), DDA (Dimethyldioctadecyl-ammonium bromide, Vaccine Design p. 157), Polyphosphazene (Vaccine Design p. 204), or alternatively oil-in-water emulsions based on mineral oil, squalene (e.g. SPT emulsion, Vaccine Design p. 147), squalene (e.g. MF59, Vaccine Design p. 183), or water-in-oil emulsions based on metabolizable oil (preferably according to WO-A-94 20071) as well as the emulsions described in U.S. Pat. No. 5,422,109. It is also possible to choose combinations of adjuvants, for example Avridine® or DDA combined with an emulsion.

These antigenic preparations, immunogenic compositions and vaccines will preferably comprise from $10^5$ to $10^8$ TCID50 of the inactivated whole virus in question.

The adjuvants for live vaccines described above can be selected from those given for the inactivated. The emulsions are preferred. To those indicated for the inactivated vaccine, there may be added those described in WO-A-9416681.

As freeze-drying stabilizer, there may be mentioned by way of example SPGA (Bovarnik et al., J. Bacteriology 59, 509, 950), carbohydrates such as sorbitol, mannitol, starch, sucrose, dextran or glucose, proteins such as albumin or casein, derivatives of these compounds, or buffers such as alkali metal phosphates.

The antigenic preparations, immunogenic compositions and vaccines according to the invention may comprise one or more active ingredients (antigens) of one or more circoviruses and/or parvoviruses according to the invention.

The applicant has, in addition, obtained the genome of four of the type II porcine circovirus isolates, identified SEQ ID NO: 1 to 4. The sequence of strain PK-15 is given as SEQ ID NO: 5. It goes without saying that the invention automatically covers the equivalent sequences, that is to say the sequences which do not change the functionality or the strain-specificity of the sequence described or of the polypeptides encoded by this sequence. There will of course be included the sequences differing by degeneracy of the code.

The invention also covers the equivalent sequences in the sense that they are capable of hybridizing with the above sequence under high stringency conditions and/or have a high homology with the strains of the invention.

These sequences and their fragments can be advantageously used for the in vitro or in vivo expression of polypeptides with the aid of appropriate vectors.

In particular, the open reading frames (ORF1-13), forming DNA fragments according to the invention, which can be used to this effect have been identified on the genomic sequence of the type II circoviruses. The invention relates to any polypeptide containing at least one of these open reading frames (corresponding amino acid sequence). Preferably, the invention relates to a protein essentially consisting of ORF4, ORF7, ORF10 or ORF13.

For the expression of subunits in vitro, as a means of expression, *E. coli* or a baculovirus will be preferably used (U.S. Pat. No. 4,745,051). The coding sequence(s) or their fragments may be integrated into the baculovirus genome (e.g. the baculovirus *Autographa californica* Nuclear Polyhedrosis Virus AcNPV) and the latter can be then propagated on insect cells, e.g. *Spodoptera frugiperda* Sf9 (deposit ATCC CRL 1711). The subunits can also be produced in eukaryotic cells such as yeasts (e.g. *Saccharomyces cerevisiae*) or mammalian cells (e.g. CHO, BHK).

The subject of the invention is also the use as subunits of the polypeptides which will be produced in vitro by these expression means, and then optionally purified according to conventional techniques. The subunit immunogenic compositions and vaccines comprise at least one polypeptide as thus obtained, or fragment, in a vehicle or diluent acceptable from the veterinary point of view and optionally an adjuvant acceptable from the veterinary point of view.

For the expression in vivo for the purpose of producing immunogenic compositions and vaccines of the recombinant live type or DNA type, the coding sequence(s) or their fragments are inserted into an appropriate expression vector under conditions allowing the expression of the polypeptide (s). As appropriate live vectors, there may be used preferably live viruses, preferably capable of multiplying in pigs, nonpathogenic for pigs (naturally nonpathogenic or rendered as such), according to techniques well known to persons skilled in the art. There may be used in particular pig herpesviruses such as Aujeszky's disease virus, porcine adenovirus, poxviruses, especially vaccinia virus, avipox virus, canarypox virus, swinepox virus. DNA vectors can also be used as vectors (WO-A-9011092,WO-A-9319813, WO-A-9421797, WO-A-9520660).

The subject of the invention is therefore also the vectors and the recombinant live type or DNA (polynucleotide) type immunogenic compositions or vaccines thus prepared, their preparation and their use, the immunogenic compositions and the vaccines comprising, in addition, a vehicle or diluent acceptable from the veterinary point of view.

By definition, a DNA immunogenic composition or vaccine comprises a DNA vector which is a circular vaccinal plasmid, supercoiled or otherwise, or a linear DNA molecule, incorporating and expressing in vivo a nucleotide sequence encoding an antigenic polypeptide.

Recombinant and DNA-type immunogenic compositions and vaccines may comprise an adjuvant.

In the context of the combined immunization or vaccination programmes, it is also possible to combine the immunization or vaccination against the porcine circovirus and the porcine parvovirus with an immunization or vaccination against other pig pathogens, in particular those which could be associated with the PMWS syndrome. The immunogenic composition or vaccine according to the invention may therefore comprise another valency corresponding to another pig pathogen chosen from PRRS (Porcine Reproductory and Respiratory Syndrome) and/or *Mycoplasma hyopneumoniae,* and/or *E. coli,* and/or Atrophic Rhinitis, and/or Pseudorabies (Aujeszky's disease) virus and/or porcine influenza and/or *Actinobacillus pleuropneumoniae* and/or Hog cholera, and combinations thereof. Preferably, the programme of immunization or vaccination and the vaccines according to the invention will combine immunizations or vaccinations against the circovirus and the parvovirus, and the PRRS (WO-A-93/07898, WO-A-94/18311, FR-A-2 709 966 ; C. Charreyre et al., Proceedings of the $15^{th}$ IPVS Congress, Birmingham, England, Jul. 5–9, 1998, p 139 ; and/or Mycoplasma hyopneumoniae (EP-A-597 852, EP-A-550 477, EP-A571 648 ; O. Martinon et al. p 157, 284, 285 and G. Reynaud et al., p 150, all in the above-referenced Proceedings of the $15^{th}$ IPVS Congress) and/or porcine influenza. It is thus possible to use any appropriate form of immunogenic composition or vaccine, in particular any available commercial vaccine, so as to combine it with the immunogenic composition or vaccine against the porcine circovirus and porcine parvovirus as described here.

The subject of the present invention is therefore also multivalent immunogenic compositions and vaccines, multivaccine kits, and combined immunization or vaccination methods which make it possible to use such combined immunization or vaccination programmes.

The invention will now be described in greater detail with the aid of nonlimiting exemplary embodiments, taken with reference to the drawing, in which:

FIG. 1: DNA sequence of the genome of the Imp. 1011-48121 strain

FIG. 2: DNA sequence of the genome of the Imp. 1011-48285 strain FIG. 3: DNA sequence of the genome of the Imp. 999 strain FIG. 4: DNA sequence of the genome of the Imp. 1010 strain FIG. 5: Alignment of the 4 sequences according to FIGS. 1 to 4 with the sequence of the PCV PK/15 strain Sequence Listing SEQ ID SEQ ID No: 1 DNA sequence of the genome of the Imp. 1011-48121 strain SEQ ID No: 2 DNA sequence of the genome of the Imp. 1011-48285 strain SEQ ID No: 3 DNA sequence of the genome of the Imp. 999 strain SEQ ID No: 4 DNA sequence of the genome of the Imp. 1010 strain SEQ ID No: 5 DNA sequence of the genome of the PK/15 strain

EXAMPLES

Example 1

Culture and Isolation of the Porcine Circovirus Strains

Tissue samples were collected in France, Canada and the USA from lung and lymph nodes of piglets. These piglets exhibited clinical signs typical of the post-weaning multisystemic wasting syndrome. To facilitate the isolation of the viruses, the tissue samples were frozen at −70° C. immediately after autopsy.

For the viral isolation, suspensions containing about 15% tissue sample were prepared in a minimum medium containing Earle's salts (EMEM, BioWhittaker UK Ltd., Wokingham, UK), penicillin (100 IU/ml) and streptomycin (100 µg/ml) (MEM-SA medium), by grinding tissues with sterile sand using a sterile mortar and pestle. This ground preparation was then taken up in MEM-SA, and then centrifuged at 3000 g for 30 minutes at +4° C. in order to harvest the supernatant.

Prior to the inoculation of the cell cultures, a volume of 100 µl of chloroform was added to 2 ml of each supernatant and mixed continuously for 10 minutes at room temperature. This mixture was then transferred to a microcentrifuge tube, centrifuged at 3000 g for 10 minutes, and then the supernatant was harvested. This supernatant was then used as inoculum for the viral isolation experiments.

All the viral isolation studies were carried out on PK/15 cell cultures, known to be uncontaminated with the porcine circovirus (PCV), pestiviruses, porcine adenoviruses and porcine parvoviruses (Allan G. et al Pathogenesis of porcine circovirus experimental infections of colostrum-deprived piglets and examination of pig foetal material. Vet. Microbiol. 1995, 44, 49–64).

The isolation of the porcine circoviruses was carried out according to the following technique:

Monolayers of PK/15 cells were dissociated by trypsinization (with a trypsin-versene mixture) from confluent cultures, and taken up in MEM-SA medium containing 15% foetal calf serum not contaminated by pestivirus (=MEM-G medium) in a final concentration of about 400,000 cells per ml. 10 ml aliquot fractions of this cell suspension were then mixed with 2 ml aliquot fractions of the inocula described above, and the final mixtures were aliquoted in 6 ml volumes in two Falcon flasks of 25 cm². These cultures were then incubated at +37° C. for 18 hours under an atmosphere containing 10% $CO_2$.

After incubation, the culture medium of the semiconfluent monolayers were treated with 300 mM D-glucosamine (Cat # G48175, Sigma-Aldrich Company Limited, Poole, UK) (Tischr I. et al., Arch. Virol., 1987 96 39–57), then incubation was continued for an additional period of 48–72 hours at +37° C. Following this last incubation, one of the two Falcons of each inoculum was subjected to 3 successive freeze/thaw cycles. The PK/15 cells of the remaining Falcon were treated with a trypsin-versene solution, resuspended in 20 ml of MEM-G medium, and then inoculated into 75 cm² Falcons at a concentration of 400,000 cells/ml. The freshly inoculated flasks were then "superinfected" by addition of 5 ml of the corresponding lysate obtained after the freeze/thaw cycles.

Example 2

Preparation of the Samples of Cell Culture for the Detection of Porcine Circoviruses By Immunofluorescence or By In Situ Hybridization A volume of 5 ml of the "superinfected" suspension was collected and inoculated into a Petri dish 55 mm in diameter containing a sterile and fat-free glass coverslip. The cultures in the flasks and on glass coverslips were incubated at +37° C. and treated with glucosamine as described in Example 1. The cultures on glass coverslips were harvested from 24 to 48 hours after the treatment with glucosamine and fixed, either with acetone for 10 minutes at room temperature, or with 10% buffered formaldehyde for 4 hours. Following this fixing, all the glass coverslips were stored at −70° C., on silica gel, before their use for the in situ hybridization studies and the immunocytochemical labelling studies.

Example 3

Techniques for the Detection of PCV Sequences By In Situ Hybridization

In situ hybridization was carried out on tissues collected from diseased pigs and fixed with formaldehyde and also on the preparations of cell cultures inoculated for the viral isolation (see Example 2) and fixed on glass coverslips.

Complete genomic probes corresponding to the PK/15 porcine circoviruses (PCV) and to the infectious chicken anaemia virus (CAV) were used. The plasmid pPCV1, containing the replicative form of the PCV genome, cloned in the form of a single 1.7 kilo base pair (kbp) insert (Meehan B. et al. Sequence of porcine circovirus DNA: affinities with plant circoviruses, J. Gen. Virol. 1997, 78, 221–227), was used as specific viral DNA source for PCV. An analogous plasmid, pCAA1, containing the 2.3 kbp replicative form of the avian circovirus CAV was used as negative control. The respective glycerol stocks of the two plasmids were used for the production and purification of the plasmids according to the alkaline lysis technique (Sambrook J. et al. Molecular cloning: A Laboratory Manual. 2nd Edition, Cold Spring Harbor Laboratory, Cold Spring Harbor, New York, 1989) so that they are then used as templates for the preparation of the probes. The circovirus probes representative of the complete genomes of PCV and of CAV were produced from the purified plasmids described above (1 µg for each probe) and from hexanucleotide primers at random using a commercial nonradioactive labelling kit ("DIG DNA labelling kit", Boehringer Mannheim, Lewes, UK) according to the supplier's recommendations.

The digoxigenin-labelled probes were taken up in a volume of 50–100 μl of sterile water before being used for the in situ hybridization.

The diseased pig tissue samples, enclosed in paraffin and fixed with formaldehyde, as well as the preparations of infected cell cultures, fixed with formaldehyde, were prepared for the detection of the PCV nucleic acids according to the following technique:

Sections 5 μm thick were cut from tissue blocks enclosed in paraffin, rendered paraffin free, and then rehydrated in successive solutions of alcohol in decreasing concentrations. The tissue sections and the cell cultures fixed with formaldehyde were incubated for 15 minutes and 5 minutes respectively at +37° C. in a 0.5% proteinase K solution in 0.05 M Tris-HCl buffer containing 5 mM EDTA (pH 7.6). The slides were then placed in a 1% glycine solution in autoclaved distilled water, for 30 seconds, washed twice with 0.01 M PBS buffer (phosphate buffered saline) (pH 7.2), and finally washed for 5 minutes in sterile distilled water. They were finally dried in the open air and placed in contact with the probes.

Each tissue/probe preparation was covered with a clean and fat-free glass coverslip, and then placed in an oven at +90° C. for 10 minutes, and then placed in contact with an ice block for 1 minute, and finally incubated for 18 hours at +37° C. The preparations were then briefly immersed in a 2× sodium citrate salt (SSC) buffer (pH 7.0) in order to remove the protective glass coverslips, and then washed twice for 5 minutes in 2× SSC buffer and finally washed twice for 5 minutes in PBS buffer.

After these washes, the preparations were immersed in a solution of 0.1 M maleic acid, 0.15 M NaCl (pH 7.5) (maleic buffer) for 10 minutes, and then incubated in a 1% solution of blocking reagent (Cat # 1096176, Boehringer Mannheim UK, Lewes, East Sussex, UK) in maleic buffer for 20 minutes at +37° C.

The preparations were then incubated with a 1/250 solution of an anti-digoxigenin monoclonal antibody (Boehringer Mannheim), diluted in blocking buffer, for 1 hour at +37° C., washed in PBS and finally incubated with a biotinylated anti-mouse immunoglobulin antibody for 30 minutes at +37° C. The preparations were washed in PBS and the endogenous peroxidase activity was blocked by treatment with a 0.5% hydrogen peroxide solution in PBS for 20 minutes at room temperature. The preparations were again washed in PBS and treated with a 3-amino-9-diethylcarbazole (AEC) substrate (Cambridge Bioscience, Cambridge, UK) prepared immediately before use.

After a final wash with tap water, the preparations were counterstained with hematoxylin, "blued" under tap water, and mounted on microscope glass coverslips with a mounting fluid (GVA Mount, Cambridge Bioscience, Cambridge, UK). The experimental controls included the use of a nonpertinent negative probe (CAV) and of a positive probe (PCV) on samples obtained from diseased pigs and from nondiseased pigs.

Example 4

Technique for the Detection of PCV By Immunofluorescence

The initial screening of all the cell culture preparations fixed with acetone was carried out by an indirect immunofluorescence technique (IIF) using a 1/100 dilution of a pool of adult pig sera. This pool of sera comprises sera from 25 adult sows from Northern Ireland and is known to contain antibodies against a wide variety of porcine viruses, including PCV: porcine parvovirus, porcine adenovirus, and PRRS virus. The IIF technique was carried out by bringing the serum (diluted in PBS) into contact with the cell cultures for one hour at +37° C., followed by two washes in PBS. The cell cultures were then stained with a 1/80 dilution in PBS of a rabbit anti-pig immunoglobulin antibody conjugated with fluorescein isothiocyanate for one hour, and then washed with PBS and mounted in glycerol buffer prior to the microscopic observation under ultraviolet light.

Example 5

Results of the In Situ Hybridization on Diseased Pig Tissues

The in situ hybridization, using a PCV genomic probe, prepared from tissues collected from French, Canadian and Californian piglets having multisystemic wasting lesions and fixed with formaldehyde, showed the presence of PCV nucleic acids associated with the lesions, in several of the lesions studied. No signal was observed when the PCV genomic probe was used on tissues collected from nondiseased pigs or when the CAV probe was used on the diseased pig tissues. The presence of PCV nucleic acid was identified in the cytoplasm and the nucleus of numerous mononuclear cells infiltrating the lesions in the lungs of the Californian piglets. The presence of PCV nucleic acid was also demonstrated in the pneumocytes, the bronchial and bronchiolar epithelial cells, and in the endothelial cells of the arterioles, the veinlets and lymphatic vessels.

In diseased French pigs, the presence of PCV nucleic acid was detected in the cytoplasm of numerous follicular lymphocytes and in the intrasinusoidal mononuclear cells of the lymph nodes. The PCV nucleic acid was also detected in occasional syncytia. Depending on these detection results, samples of Californian pig lungs, French pig mesenteric lymph nodes, and Canadian pig organs were selected for the purpose of isolating new porcine circovirus strains.

Example 6

Results of the Cell Culture of the New Porcine Circovirus Strains and Detection By Immunofluorescence No cytopathic effect (CPE) was observed in the cell cultures inoculated with the samples collected from French piglets (Imp.1008 strain), Californian piglets (Imp.999 strain) and Canadian piglets (Imp.1010 strain) showing clinical signs of multisystemic wasting syndrome. However, immunolabelling of the preparations obtained from the inoculated cell cultures, after fixing using acetone and with a pool of pig polyclonal sera, revealed nuclear fluorescence in numerous cells in the cultures inoculated using the lungs of Californian piglets (Imp.999 strain), using the mediastinal lymph nodes of French piglets (Imp.1008 strain), and using organs of Canadian piglets (Imp.1010 strain).

Example 7

Extraction of the Genomic DNA of the Porcine Circoviruses

The replicative forms of the new strains of porcine circoviruses (PCV) were prepared using infected PK/15 cell cultures (see Example 1) (10 Falcons of 75 cm$^2$) harvested after 72–76 hours of incubation and treated with glucosamine, as described for the cloning of the replicative form of CAV (Todd. D. et al. Dot blot hybridization assay for chicken anaemia agent using a cloned DNA probe. J. Clin. Microbiol. 1991, 29, 933–939). The double-stranded DNA of these replicative forms was extracted according to a modification of the Hirt technique (Hirt B. Selective extraction of polyoma virus DNA from infected cell cultures, J. Mol. Biol. 1967, 36, 365–369), as described by Molitor (Molitor T. W. et al. Porcine parvovirus DNA: characterization of the genomic and replicative form DNA of two virus isolates, Virology, 1984, 137, 241–254).

Example 8

Restriction Map of the Replicative Form of the Genome of the Porcine Circovirus Imp.999 Strain The DNA (1–5 µg) extracted according to the Hirt technique was treated with S1 nuclease (Amersham) according to the supplier's recommendations, and then this DNA was digested with various restriction enzymes (Boehringer Mannheim, Lewis, East Sussex, UK) and the products of digestion were separated by electrophoresis on a 1.5% agarose gel in the presence of ethidium bromide as described by Todd et al. (Purification and biochemical characterization of chicken anemia agent. J. Gen. Virol. 1990, 71, 819–823). The DNA extracted from the cultures of the Imp.999 strain possess a unique EcoRI site, 2 SacI sites and do not possess any PstI site. This restriction profile is therefore different from the restriction profile shown by the PCV PK/15 strain (Meehan B. et al. Sequence of porcine circovirus DNA; affinities with plant circoviruses, 1997 78, 221–227) which possess in contrast a PstI site and do not possess any EcoRI site.

Example 9

Cloning of the Genome of the Porcine Circovirus Imp.999 Strain

The restriction fragment of about 1.8 kbp generated by digestion of the double-stranded replicative form of the PCV Imp.999 strain with the restriction enzyme EcoRI was isolated after electrophoresis on a 1.5% agarose gel (see Example 3) using a Qiagen commercial kit (QIAEXII Gel Extraction Kit, Cat # 20021, QIAGEN Ltd., Crawley, West Sussex, UK). This EcoRI-EcoRI restriction fragment was then ligated with the vector pGEM-7 (Promega, Medical Supply Company, Dublin, Ireland), previously digested with the same restriction enzymes and dephosphorylated, according to standard cloning techniques (Sambrook J. et al. Molecular cloning: A Laboratory Manual, 2nd Edition, Cold Spring Harbor Laboratory, Cold Spring Harbor, New York, 1989). The plasmids obtained were transformed into an *Escherichia coli* JM109 host strain (Stratagene, La Jolla, USA) according to standard techniques. The EcoRI-EcoRI restriction fragment of the PCV Imp.999 strain was also cloned into the EcoRI site of the vector pBlueScript SK+ (Stratagene Inc. La Jolla, USA). Among the clones obtained for each host strain, at least 2 clones containing the fragments of the expected size were selected. The clones obtained were then cultured and the plasmids containing the complete genome of the Imp.999 strain were purified in a small volume (2 ml) or in a large volume (250 ml) according to standard plasmid preparation and purification techniques.

Example 10

Sequencing of a Genomic DNA (Double-Stranded Replicative Form) of the PCV Imp.999 Strain The nucleotide sequence of 2 EcoRI Imp.999 clones (clones pGEM-7/2 and pGEM-7/8) was determined according to Sanger's dideoxynucleotide technique using the sequencing kit "AmpliTaq DNA polymerase FS" (Cat # 402079 PE Applied Biosystems, Warrington, UK) and an Applied BioSystems AB1373A automatic sequencing apparatus according to the supplier's recommendations. The initial sequencing reactions were carried out with the M13 "forward" and "reverse" universal primers. The following sequencing reactions were generated according to the "DNA walking" technique. The oligonucleotides necessary for these subsequent sequencings were synthesized by Life Technologies (Inchinnan Business Park, Paisley, UK).

The sequences generated were assembled and analysed by means of the MacDNASIS version 3.2 software (Cat # 22020101, Appligene, Durham, UK). The various open reading frames were analysed by means of the BLAST algorithm available on the "National Center for Biotechnology Information" (NCBI, Bethesda, Md., USA) server.

The complete sequence (EcoRI-EcoRI fragment) is presented in SEQ ID No: 3 (FIG. 3). It gives the total sequence of this strain, which was made to start arbitrarily at the beginning of the EcoRI site, that is to say the G as the first nucleotide.

The procedure was carried out in a similar manner for obtaining the sequence of the other three isolates according to the invention (see SEQ ID No: 1, 2 and 4 and FIGS. 1, 2 and 4).

The size of the genome of these four strains is:

| Imp. 1011-48121 | 1767 nucleotides |
| Imp. 1011-48285 | 1767 nucleotides |
| Imp. 999 | 1768 nucleotides |
| Imp. 1010 | 1768 nucleotides |

Example 11

Analysis of the Sequence of the PCV Imp.999 Strain

When the sequence generated from the Imp.999 strain was used to test for homology with respect to the sequences contained in the GenBank databank, the only significant homology which was detected is a homology of about 76% (at nucleic acid level) with the sequence of the PK/15 strain (accession numbers Y09921 and U49186) (see FIG. 5).

At amino acid level, the test for homology in the translation of the sequences in the 6 phases with the databanks (BLAST X algorithm on the NABI server) made it possible to demonstrate a 94% homology with the open reading frame corresponding to the theoretical replicase of the BBTV virus similar to the circoviruses of plants (GenBank identification number 1841515) encoded by the GenBank U49186 sequence.

No other sequence contained in the databanks show significant homology with the sequence generated from the PCV Imp.999 strain.

Analysis of the sequences obtained from the Imp.999 strain cultured using lesions collected from Californian piglets having clinical signs of the multisystemic wasting syndrome shows clearly that this viral isolate is a new porcine circovirus strain.

Example 12

Comparative Analysis of the Sequences

The alignment of the nucleotide sequences of the 4 new PCV strains was made with the sequence of the PCV PK/15 strain (FIG. 5). A homology matrix taking into account the four new strains and the previous PK/15 strain was established. The results are the following:

|   | 1: Imp. 1011-48121 | | | |
|---|---|---|---|---|
|   | 2: Imp. 1011-48285 | | | |
|   | 3: Imp. 999 | | | |
|   | 4: Imp. 1010 | | | |
|   | 5: PK/15 | | | |
|   | 1 | 2 | 3 | 4 | 5 |
| 1 | 1.0000 | 0.9977 | 0.9615 | 0.9621 | 0.7600 |
| 2 |  | 1.0000 | 0.9621 | 0.9632 | 0.7594 |
| 3 |  |  | 1.0000 | 0.9949 | 0.7560 |
| 4 |  |  |  | 1.0000 | 0.7566 |
| 5 |  |  |  |  | 1.0000 |

The homology between the two French strains Imp. 1011-48121 and Imp. 1011-48285 is greater than 99% (0.9977).

The homology between the two North American strains Imp. 999 and Imp. 1010 is also greater than 99% (0.9949). The homology between the French strains and the North American strains is slightly greater than 96%.

The homology between all these strains and PK/15 falls at a value between 75 and 76%.

It is deduced therefrom that the strains according to the invention are representative of a new type of porcine circovirus, distinct from the type represented by the PK/15 strain. This new type, isolated from pigs exhibiting the PMWS syndrome, is called type II porcine circovirus, PK/15 representing type I. The strains belonging to this type II exhibit remarkable nucleotide sequence homogeneity, although they have in fact been isolated from very distant geographical regions.

Example 13

Analysis of the Proteins Encoded by the Genome of the New PCV Strains

The nucleotide sequence of the Imp. 1010 isolate was considered to be representative of the other circovirus strains associated with the multi-systemic wasting syndrome. This sequence was analysed in greater detail with the aid of the BLASTX algorithm (Altschul et al. J. Mol. Biol. 1990. 215. 403–410) and of a combination of programs from the set of MacVector 6.0 software (Oxford Molecular Group, Oxford OX4 4GA, UK). It was possible to detect 13 open reading frames (or ORFs) of a size greater than 20 amino acids on this sequence (circular genome). These 13 ORFs are the following:

| Name | Start | End | Strand | Size of the ORF (nucleotides (nt)) | Protein size (amino acids (aa)) |
|---|---|---|---|---|---|
| ORF1 | 103 | 210 | sense | 108 nt | 35 aa |
| ORF2 | 1180 | 1317 | sense | 138 nt | 45 aa |
| ORF3 | 1363 | 1524 | sense | 162 nt | 53 aa |
| ORF4 | 398 | 1342 | sense | 945 nt | 314 aa |
| ORF5 | 900 | 1079 | sense | 180 nt | 59 aa |
| ORF6 | 1254 | 1334 | sense | 81 nt | 26 aa |
| ORF7 | 1018 | 704 | antisense | 315 nt | 104 aa |
| ORF8 | 439 | 311 | antisense | 129 nt | 42 aa |
| ORF9 | 190 | 101 | antisense | 90 nt | 29 aa |

-continued

| Name | Start | End | Strand | Size of the ORF (nucleotides (nt)) | Protein size (amino acids (aa)) |
|---|---|---|---|---|---|
| ORF10 | 912 | 733 | antisense | 180 nt | 59 aa |
| ORF11 | 645 | 565 | antisense | 81 nt | 26 aa |
| ORF12 | 1100 | 1035 | antisense | 66 nt | 21 aa |
| ORF13 | 314 | 1381 | antisense | 702 nt | 213 aa |

The positions of the start and end of each ORF refer to the sequence presented in FIG. 4 (SEQ ID No. 4), of the genome of strain 1010. The limits of ORFs 1 to 13 are identical for strain 999. They are also identical for strains 1011-48121 and 1011-48285, except for the ORFs 3 and 13:

ORF3 1432-1539, sense, 108 nt, 35aa

ORF13 314-1377, antisense, 705 nt, 234 aa.

Among these 13 ORFs, 4 have a significant homology with analogous ORFs situated on the genome of the cloned virus PCV PK-15. Each of the open reading frames present on the genome of all the circovirus isolates associated with the multisystemic wasting syndrome was analysed. These 4 ORFs are the following:

| Name | Start | End | Strand | Size of the ORF (nt) | Protein size (aa) | Molecular mass |
|---|---|---|---|---|---|---|
| ORF4 | 398 | 1342 | sense | 945 nt | 314 aa | 37.7 kDa |
| ORF7 | 1018 | 704 | antisense | 315 nt | 104 aa | 11.8 kDa |
| ORF10 | 912 | 733 | antisense | 180 nt | 59 aa | 6.5 kDa |
| ORF13 | 314 | 1381 | antisense | 702 nt | 233 aa | 27.8 kDa |

The positions of the start and end of each ORF refer to the sequence presented in FIG. 4 (SEQ ID No. 4). The size of the ORF (in nucleotides=nt) includes the stop codon.

The comparison between the genomic organization of the PCV Imp. 1010 and PCV PK-15 isolates allowed the identification of 4 ORFs preserved in the genome of the two viruses. The table below presents the degrees of homology observed:

| ORF Imp. 1010/ORF PVC PK-15 | Percentage homology |
|---|---|
| ORF4/ORF1 | 86% |
| ORF13/ORF2 | 66.4% |
| ORF7/ORF3 | 61.5% (at the level of the overlap (104 aa)) |
| ORF10/ORF4 | 83% (at the level of the overlap (59 aa)) |

The greatest sequence identity was observed between ORF4 Imp. 1010 and ORF1 PK-15 (86% homology). This was expected since this protein is probably involved in the replication of the viral DNA and is essential: for the viral replication (Meehan et al. J. Gen. Virol. 1997. 78. 221–227; Mankertz et al. J. Gen. Virol. 1998. 79. 381–384).

The sequence identity between ORF13 Imp. 1010 and ORF2 PK-15 is less strong (66.4% homology), but each of these two ORFs indeed exhibits a highly conserved N-terminal basic region which is identical to the N-terminal region of the major structural protein of the CAV avian circovirus (Meehan et al. Arch. Virol. 1992. 124. 301–319). Furthermore, large differences are observed between ORF7 Imp. 1010 and ORF3 PK-15 and between ORF10 Imp. 1010 and ORF4 PK-15. In each case, there is a deletion of the C-terminal region of the ORF7 and ORF10 of the Imp. 1010 isolate when they are compared with ORF3 and ORF4 of PCV PK-15. The greatest sequence homology is observed at the level of the N-terminal regions of ORF7/ORF3 (61.5% homology at the level of the overlap) and of ORF10/ORF4 (83% homology at the level of the overlap).

It appears that the genomic organization of the porcine circovirus is quite complex as a consequence of the extreme compactness of its genome. The major structural protein is probably derived from splicing between several reading frames situated on the same strand of the porcine circovirus genome. It can therefore be considered that any open reading frame (ORF1 to ORF13) as described in the table above can represent all or part of an antigenic protein encoded by the type II porcine circovirus and is therefore potentially an antigen which can be used for specific diagnosis and/or for vaccination. The invention therefore relates to any protein comprising at least one of these ORFs. Preferably, the invention relates to a protein essentially consisting of ORF4, ORF7, ORF10 or ORF13.

Example 14

Infectious Character of the PCV Genome Cloned From the New Strains

The plasmid pGEM-7/8 containing the complete genome (replicative form) of the Imp.999 isolate was transfected into PK/15 cells according to the technique described by Meehan B. et al. (Characterization of viral DNAs from cells infected with chicken anemia agent: sequence analysis of the cloned replicative form and transfection capabilities of cloned genome fragments. Arch. Virol. 1992, 124, 301–319). Immunofluorescence analysis (see Example 4) carried out on the first passage after transfection on noncontaminated PK/15 cells have shown that the plasmid of the clone pGEM7/8 was capable of inducing the production of infectious PCV virus. The availability of a clone containing an infectious PCV genetic material allows any useful manipulation on the viral genome in order to produce modified PCV viruses (either attenuated in pigs, or defective) which can be used for the production of attenuated or recombinant vaccines, or for the production of antigens for diagnostic kits.

Example 15

Production of PCV Antigens by In Vitro Culture

The culture of the noncontaminated PK/15 cells and the viral multiplication were carried out according to the same methods as in Example 1. The infected cells are harvested after trypsinization after 4 days of incubation at 37° C. and enumerated. The next passage is inoculated with 400,000 infected cells per ml.

Example 16

Inactivation of the Viral Antigens

At the end of the viral culture, the infected cells are harvested and lysed using ultrasound (Branson Sonifier) or with the aid of a rotor-stator type colloid mill (UltraTurrax, IKA). The suspension is then centrifuged at 3700 g for 30 minutes. The viral suspension is inactivated with 0.1% ethyleneimine for 18 hours at +37° C. or with 0.5% beta-propiolactone for 24 hours at +28° C. If the virus titre before inactivation is inadequate, the viral suspension is concentrated by ultrafiltration using a membrane with a 300 kDa cut-off (Millipore PTMK300). The inactivated viral suspension is stored at +5° C.

Example 17

Preparation of the Vaccine in the Form of an Emulsion Based on Mineral Oil

The vaccine is prepared according to the following formula:

suspension of inactivated porcine circovirus: 250 ml

Montanide® ISA 70 (SEPPIC): 750 ml

The aqueous phase and the oily phase are sterilized separately by filtration. The emulsion is prepared by mixing and homogenizing the ingredients with the aid of a Silverson turbine emulsifier.

One vaccine dose contains about $10^{7.5}$ TCID50. The volume of one vaccine dose is 0.5 ml for administration by the intradermal route, and 2 ml for administration by the intramuscular route.

This vaccine is used in a vaccination programme against the multisystemic wasting syndrome in combination with the Parvovax® vaccine.

Example 18

Preparation of the Vaccine in the Form of a Metabolizable Oil-Based Emulsion

The vaccine is prepared according to the following formula:

suspension of inactivated porcine circovirus: 200 ml

Dehymuls HRE 7 (Henkel): 60 ml

Radia 7204 (Oleofina): 740 ml

The aqueous phase and the oily phase are sterilized separately by filtration. The emulsion is prepared by mixing and homogenizing the ingredients with the aid of a Silverson turbine emulsifier.

One vaccine dose contains about $10^{7.5}$ TCID50. The volume of one vaccine dose is 2 ml for administration by the intramuscular route.

This vaccine is used in a vaccination programme against the multisystemic wasting syndrome in combination with the Parvova® vaccine.

Example 19

The Indirect Immofluorescence Results in Relation to the US and French PCV Virus Strains and to the PK/15 Contaminant With a Hyperimmune Serum (PCV-T), a Panel of Monoclonal Antibodies F99 Prepared From PK/15 and a Hyperimmune Serum Prepared From the Canadian Strain (PCV-C)

| VIRUS | PK/15 | USA | France |
|---|---|---|---|
| PCV-T antiserum | ≧6400 | 200 | 800 |
| PCV-C antiserum | 200 | ≧6.400 | ≧6.400 |
| F99 1H4 | ≧10000 | <100 | 100 |
| F99 4B10 | ≧10000 | <100 | <100 |
| F99 2B7 | ≧10000 | 100 | <100 |
| F99 2E12 | ≧10000 | <100 | <100 |

-continued

| VIRUS | PK/15 | USA | France |
|---|---|---|---|
| F99 1C9 | ≧10000 | <100 | 100 |
| F99 2E1 | ≧10000 | <100 | <100 |
| F99 1H4 | ≧10000 | 100 | <100 |

* Reciprocal of the last dilution of the serum or of the monoclonal antibody which gives a positive reaction in indirect immunofluorescence.

Example 20

Experimental Production of the Porcine Multisystemic Wasting Syndrome—Protocol 1

Three-day old gnotobiotic piglets obtained by caesarean and kept in an isolating unit were inoculated with virus solutions of PCV. The type II PCV viruses used were the Imp 1010 isolate and the virus obtained from lymph node homogenates obtained from diseased pigs. Five groups were formed. The piglets were all inoculated at the age of three days by the oronasal route with 1.5 ml of virus solution according to the following scheme:

| Group | Number | Virus | Dose |
|---|---|---|---|
| A | 6 | Lymph node homogenate | ND |
| B | 5 | Imp. 1010 (low passage) | $10^2$ TCID50 |
| C | 4 | Imp. 1010 (high passage) | $10^2$ TCID50 |
| D | 2 | Lysate of PK15 cells free of PCV virus | — |
| E | 3 | — | — |

Results of the experimental challenge: During the 5-week observation period, the piglets did not develop clinical signs, apart from one animal in group B which showed substantial exhaustion. At autopsy, the pigs in groups A, B and C exhibit hyperplasia of the lymph nodes (size 2 to 10 times greater than that for the animals in groups D and E), in particular of the submaxillary, bronchial, mesenteric, iliac and femoral ganglia. This hyperplasia is linked to a considerable expansion of the cortical zones by infiltration by monocytes and macrophages. The piglets in groups A, B and C also exhibit hyper-plasia of the bronchial lymphoid tissue. One piglet in each of groups A, B and C has pneumonia. The piglet in group B, which exhibited substantial exhaustion, and one piglet in group A have a gastric ulcer. Moreover, all the animals in groups A, B and C have myositis in the muscular tunica of the stomach and of the intestine. Most of the animals in groups A, B and C have myocarditis, multifocal hepatitis with lymphocyte, macrophage and eosinophile infiltration, as well as cortical and medullary interstitial nephritis. One piglet in group C has a liver whose size is bigger than normal, with disseminated clear foci at its surface. No lesion was observed in the piglets in groups D and E. Circovirus was isolated from the organs of pigs in groups A, B and C.

Example 21

Experimental Reproduction of the Porcine Multisystemic Wasting Syndrome—Protocols 2 and 1

Conventional piglets, but isolated from their mother from birth, were inoculated with viral solutions of type II PCV, of porcine parvovirus, or with a mixture of the two viruses. The type II PCV viruses used were the Imp. 1010 and Imp. 1011 isolates (strain 48121). The PPV virus used is an isolate of Canadian origin, Imp. 1005. This virus has a sequence (⅓ of the sequenced genome) which is identical to that of other known porcine parvovirus strains (PPV strain NADL-2 and Kresse strain). Two experimental protocols were carried out.

Protocol 2

Three groups were formed with 3-day-old piglets. The piglets were all inoculated by the oronasal route with 1 ml of viral solution according to the following scheme:

| Group | Number | Virus | Dose |
|---|---|---|---|
| A | 5 | Imp. 1010 | $10^7$ TCID50 |
| B | 5 | Imp. 1010 + Imp. 1005 | $5 \times 10^6$ TCID50 |
| C (control) | 2 | — | — |

Results of the experimental challenge: Group A: 2 piglets died 21 days after the inoculation and one piglet was humanely killed 24 days after the inoculation. Group B: 1 piglet died 23 days after the inoculation and one piglet was humanely killed 24 days after the inoculation. The autopsies carried out on the piglets that died following an infection showed the presence of substantial macroscopic lesions: presence of fluid in the pleural cavity, lung oedema, haemorrhages in the kidneys, whitish lesions in the form of a pin head on the kidneys, hepatic necrosis. These lesions are identical to those observed in the field cases. The autopsies carried out on the sacrificed piglets did not show macroscopic lesions. The histological examinations performed on organs removed from the piglets in groups A and B which died following an infection, as well as in the sacrificed pigs in these 2 groups, showed a typical and complete pattern of the lesions of porcine multisystemic wasting syndrome which are observed in animals in the field: hepatic necrosis, necrosis of the lymph nodes, pancreatic necrosis, focal necrosis and severe haemorrhages in the kidneys, presence of syncytia in the lungs, severe necrosis of the hepatocytes with the presence of nuclear inclusions. It should be noted that a massive quantity of PCV antigen was found in all these lesions (dead or sacrificed pigs), but that the presence of PPV antigen could not be detected in these same lesions. No lesion could be detected in the control piglets in group C.

Protocol 3

Four groups were formed with 4-week-old piglets. The pigs were all inoculated by the oronasal route with 1 ml of viral solution according to the following scheme:

| Group | Number | Virus | Dose |
|---|---|---|---|
| A (control) | 2 | — | — |
| B | 4 | Imp. 1005 (PPV) | $10^{5.3}$ TCID50 |
| C | 4 | Imp. 1011 (PCV) | $10^5$ TCID50 |
| D | 4 | Imp. 1005 + Imp. 1011 | $10^5 + 5 \times 10^4$ TCID50 |

Results of the experimental challenge: 1 "control" piglet and 2 piglets in each experimental group (B, C and D) were humanely killed and subjected to autopsy 2 weeks after inoculation. Significant immunohistological lesions were observed in the two piglets in group D (PCV+PPV coinfection). It should be noted that it was not possible to detect the presence of porcine parvovirus in these lesions, although a seroconversion in relation to the porcine parvovirus was observed in all the pigs in group D. No macroscopic or histological lesion could be observed in the control piglet and in the piglets in the other groups. It therefore appears that the PCV+PPV combination makes it possible to reproduce histological lesions typical of the porcine multisystemic wasting syndrome. Following these two experimental protocols, it can be observed that the inoculation of PCV alone, as a PCV+PPV mixture, leads to a more or less severe reproduction of the porcine multisystemic wasting syndrome, but only the porcine circovirus can be detected in the lesions. By contrast, an experimental infection with PPV alone (group B of protocol 3) does not allow macroscopic or histological lesions to be induced; however, in the presence of PCV, the appearance of lesions is observed in 4-week-old pigs (group D of protocol 3).

What is claimed is:

1. An immunogenic composition for eliciting an immunological response against porcine parvovirus and porcine circovirus comprising at least one porcine parvovirus antigen and at least one porcine circovirus antigen, and a veterinarily acceptable vehicle or excipient.

2. The immunogenic composition of claim 1 wherein the porcine circovirus antigen comprises at least one porcine circovirus type II antigen.

3. The immunogenic composition of claim 2 wherein the porcine circovirus type II antigen is at least one antigen of a porcine circovirus type II deposited at the ECACC selected from group consisting of: porcine circovirus type II accession No. V97100219, porcine circovirus type II accession No. V97100218, porcine circovirus type II accession No. V97100217, porcine circovirus type II accession No. V98011608, and porcine circovirus type II accession No. V98011609.

4. The immunogenic composition of claim 2 wherein the porcine circovirus type II antigen is an attenuated virus porcine circovirus type II.

5. The immunogenic composition of claim 4 further comprising a veterinarily acceptable adjuvant.

6. The immunogenic composition of claim 4 further comprising a freeze-drying stabilizer.

7. The immunogenic composition of claim 2 wherein the porcine circovirus type II antigen is an inactivated porcine circovirus type II.

8. The immunogenic composition of claim 7 further comprising a veterinarily acceptable adjuvant.

9. The immunogenic composition of claim 2 wherein the composition further comprises an additional antigen of another porcine pathogen.

10. The immunogenic composition of claim 9 wherein the additional antigen of another porcine pathogen is selected from the group consisting of: an antigen of PRRS virus, an antigen of Mycoplasma hypopneumoniae, an antigen of Actinobacillus pleuropneumoniae, an antigen of E. coli, an antigen of Atrophic Rhinitis, an antigen of Pseudorabies virus, an antigen of Hog cholera, an antigen of Swine Influenza, and combinations thereof.

11. The immunogenic composition of claim 10 wherein the additional antigen of another porcine pathogen is an antigen of PRRS virus.

12. The immunogenic composition of claim 2 wherein the porcine circovirus type II antigen comprises an antigen encoded by a porcine circovirus type II open reading frame (ORF) selected from the group consisting of ORFs 1, 2, 3, 4, 5, 6, 7, 8, 9, 10, 11, 12, and 13.

13. The immunogenic composition of claim 2 wherein the porcine circovirus type II antigen comprises an antigen encoded by a porcine circus type II open reading frame (ORF) selected from the group consisting of ORFs 4, 7, 10, and 13.

14. The immunogenic composition of claim 2 wherein the porcine circovirus type II antigen comprises a vector that contains and expresses in vivo an antigen encoded by a porcine circovirus type II open reading frame (ORF) selected from the group consisting of ORFs 1, 2, 3, 4,5,6,7, 8, 9, 10,11, 12, and 13.

15. The immunogenic composition of claim 14 wherein the vector is selected from the group consisting of a DNA plasmid, a linear DNA molecule, and a recombinant virus.

16. The immunogenic composition of claim 15 wherein the recombinant virus is selected from the group consisting of pig herpes virus, porcine adenovirus, and poxvirus.

17. The immunogenic composition of claim 16 wherein the recombinant virus is selected from the group consisting of Aujesky's disease virus, vaccinia virus, avipox virus, canarypox virus, and swine pox virus.

18. The immunogenic composition of claim 2 wherein the porcine circovirus type II antigen comprises a vector that contains and expresses in vivo an antigen encoded by a porcine circovirus type II open reading frame (ORF) selected from the group consisting of ORFs 4, 7, 10, and 13.

19. The immunogenic composition of claim 18 wherein the vector is selected from the group consisting of a DNA plasmid, a linear DNA molecule, and a recombinant virus.

20. The immunogenic composition of claim 19 wherein the recombinant virus is selected from the group consisting of pig herpes virus, porcine adenovirus, and poxvirus.

21. The immunogenic composition of claim 20 wherein the recombinant virus is selected from the group consisting of Aujesky's disease virus, vaccinia virus, avipox virus, canarypox virus, and swine pox virus.

22. The immunogenic composition of claim 1 wherein the porcine parvovirus antigen is selected from the group consisting of an attenuated porcine parvovirus, an inactivated porcine parvovirus, a subunit of porcine parvovirus, and a vector that contains and expresses in vivo a nucleic acid molecule encoding the porcine parvovirus antigen; and the porcine circovirus antigen is selected from the group consisting of an attenuated porcine circovirus, an inactivated porcine circovirus, a subunit of porcine circovirus, and a vector that contains and expresses in vivo a nucleic acid molecule encoding the porcine circovirus antigen.

23. The immunogenic composition of claim 22 wherein the vector that contains and expresses in vivo a nucleic acid molecule encoding the porcine parvovirus antigen is selected from the group consisting of a DNA plasmid, a linear DNA molecule, and a recombinant virus; and, the vector that contains and expresses in vivo a nucleic acid molecule encoding the porcine circovirus antigen is selected from the group consisting of a DNA plasmid, a linear DNA molecule, and a recombinant virus.

24. The immunogenic composition of claim 1 wherein the composition further comprises an additional antigen of another porcine pathogen.

25. The immunogenic composition of claim 24 wherein the additional antigen of another porcine pathogen is selected from the group consisting of: an antigen of PRRS virus, an antigen of *Mycoplasma hypopneumoniae,* an antigen of *Actinobacillus pleuropneumoniae,* an antigen of *E. coli,* an antigen of Atrophic Rhinitis, an antigen of Pseudorabies virus, an antigen of Hog cholera, an antigen of Swine Influenza, and combinations thereof.

26. The immunogenic composition of claim 24 wherein the additional antigen of another porcine pathogen is an antigen of PRRS virus.

27. The immunogenic composition according to claim 1 wherein the antigen of porcine circovirus comprises antigens of a plurality of porcine circoviruses.

28. A method for inducing an immunological response against porcine parvovirus and porcine circovirus comprising administering to a porcine an immunogenic composition as claimed in any one of claims 1–27.

29. A kit for preparing the immunogenic composition of claim 1 comprising (i) the at least one porcine parvovirus antigen and (ii) the at least one porcine circovirus antigen, wherein (i) and (ii) are packaged separately.

30. The kit of claim 29 wherein the porcine circovirus antigen comprises at least one porcine circovirus type II antigen.

* * * * *

UNITED STATES PATENT AND TRADEMARK OFFICE
CERTIFICATE OF CORRECTION

PATENT NO.    : 6,217,883 B1
DATED         : April 17, 2001
INVENTOR(S)   : Gordon Moore Allan et al.

It is certified that error appears in the above-identified patent and that said Letters Patent is hereby corrected as shown below:

Item [75] Inventors: change "ChrJistophe" to -- Christophe --

Signed and Sealed this

Second Day of October, 2001

Attest:

*Nicholas P. Godici*

NICHOLAS P. GODICI
*Attesting Officer*   *Acting Director of the United States Patent and Trademark Office*

UNITED STATES PATENT AND TRADEMARK OFFICE
CERTIFICATE OF CORRECTION

PATENT NO. : 6,217,883 B1  
DATED : April 17, 2001  
INVENTOR(S) : Allan et al.

Page 1 of 1

It is certified that error appears in the above-identified patent and that said Letters Patent is hereby corrected as shown below:

<u>Title page,</u>  
Item [54], change "PARAVOVIRUS" to -- PARVOVIRUS --

Item [75], change "Lyons, France" to -- Lyon, France --

Item [73] Assignee: change "Lyons (FR)" to -- Lyon (FR) --

Signed and Sealed this

Eighteenth Day of December, 2001

Attest:

Attesting Officer

JAMES E. ROGAN  
*Director of the United States Patent and Trademark Office*

UNITED STATES PATENT AND TRADEMARK OFFICE
Certificate

Patent No. 6,217,883 B1                                                                                         Patented: April 17, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gordon Moore Allan, Belfast, GB; Brian Martin Meehan, Belfast, GB; John Albert Ellis, Saskatchewan, CA; George Steven Krakowka, Columbus, OH; Jean-Christophe Francis Audonnet, Lyon, FR; and Francis McNeilly, Newtonards, GB.

Signed and Sealed this Twenty-fifth Day of March 2003.

JAMES C. HOUSEL
                                                            *Supervisory Patent Examiner*
                                                                         Art Unit 1648

SEQUENCE LISTING

<160> NUMBER OF SEQ ID NOS: 5

<210> SEQ ID NO: 1
<211> LENGTH: 1767
<212> TYPE: DNA
<213> ORGANISM: Porcine circovirus

<400> SEQUENCE: 1

| | | | | | |
|---|---|---|---|---|---|
| aattcaacct | taacctttct | tattctgtag | tattcaaagg | gcacagagcg | ggggtttgag | 60 |
| cccctcctg | ggggaagaaa | gtcattaata | ttgaatctca | tcatgtccac | cgcccaggag | 120 |
| ggcgttctga | ctgtggttcg | cttgacagta | tatccgaagg | tgcgggagag | gcgggtgttg | 180 |
| aagatgccat | ttttccttct | ccagcggtaa | cggtggcggg | ggtggacgag | ccaggggcgg | 240 |
| cggcggagga | tctggccaag | atggctgcgg | gggcggtgtc | ttcttctccg | gtaacgcctc | 300 |
| cttggatacg | tcatatctga | aaacgaaaga | agtgcgctgt | aagtattacc | agcgcacttc | 360 |
| ggcagcggca | gcacctcggc | agcacctcag | cagcaacatg | ccgagcaaga | agaatggaag | 420 |
| aagcggaccc | caacccata | aaaggtgggt | gttcactctg | aataatcctt | ccgaagacga | 480 |
| gcgcaagaaa | atacgggatc | ttccaatatc | cctatttgat | tattttattg | ttggcgagga | 540 |
| gggtaatgag | gaaggacgaa | cacctcacct | ccaggggttc | gctaattttg | tgaagaagca | 600 |
| gactttaat | aaagtgaagt | ggtatttggg | tgcccgctgc | cacatcgaga | aagcgaaagg | 660 |
| aacagatcag | cagaataaag | aatactgcag | taaagaaggc | aacttactga | tggagtgtgg | 720 |
| agctcctaga | tctcaggac | aacggagtga | cctgtctact | gctgtgagta | ccttgttgga | 780 |
| gagcgggagt | ctggtgaccg | ttgcagagca | gcaccctgta | acgtttgtca | gaaatttccg | 840 |
| cgggctggct | gaacttttga | aagtgagcgg | gaaaatgcag | aagcgtgatt | ggaagactaa | 900 |
| tgtacacgtc | attgtgggc | cacctgggtg | tggtaaaagc | aaatgggctg | ctaattttgc | 960 |
| agacccggaa | accacatact | ggaaaccacc | tagaaacaag | tggtgggatg | gttaccatgg | 1020 |
| tgaagaagtg | gttgttattg | atgactttta | tggctggctg | ccctgggatg | atctactgag | 1080 |
| actgtgtgat | cgatatccat | tgactgtaga | gactaaaggt | ggaactgtac | cttttttggc | 1140 |
| ccgcagtatt | ctgattacca | gcaatcagac | cccgttggaa | tggtactcct | caactgctgt | 1200 |
| cccagctgta | gaagctcttt | atcggaggat | tacttccttg | gtattttgga | agaatgctac | 1260 |
| agaacaatcc | acggaggaag | ggggccagtt | cgtcaccctt | tccccccat | gccctgaatt | 1320 |
| tccatatgaa | ataaattact | gagtcttttt | tatcacttcg | taatggtttt | tattattcat | 1380 |
| taagggttaa | gtgggggtc | tttaagatta | aattctctga | attgtacata | catggttaca | 1440 |
| cggatattgt | attcctggtc | gtatatactg | ttttcgaacg | cagtgccgag | gcctacgtgg | 1500 |
| tctacatttc | cagcagtttg | tagtctcagc | cacagctggt | ttcttttgtt | gtttggttgg | 1560 |
| aagtaatcaa | tagtggaatc | taggacaggt | ttgggggtaa | agtagcggga | gtggtaggag | 1620 |
| aagggctggg | ttatggtatg | gcgggaggag | tagtttacat | agggggtcata | ggtgagggct | 1680 |
| gtggcctttg | ttacaaagtt | atcatctaga | ataacagcac | tggagcccac | tcccctgtca | 1740 |

-continued

```
ccctgggtga tcggggagca gggccag                                      1767

<210> SEQ ID NO: 2
<211> LENGTH: 1767
<212> TYPE: DNA
<213> ORGANISM: Porcine circovirus

<400> SEQUENCE: 2
aattcaacct taacctttct tattctgtag tattcaaagg gcacagagcg ggggtttgag     60 cccccctcctg ggggaagaaa gtcattaata ttgaatctca tcatgtccac cgcccaggag   120
ggcgttttga ctgtggttcg cttgacagta tatccgaagg tgcgggagag gcgggtgttg   180
aagatgccat ttttccttct ccagcggtaa cggtggcggg ggtggacgag ccaggggcgg   240
cggcggagga tctggccaag atggctgcgg gggcggtgtc ttcttctccg gtaacgcctc   300
cttggatacg tcatatctga aaacgaaaga agtgcgctgt aagtattacc agcgcacttc   360
ggcagcggca gcacctcggc agcacctcag cagcaacatg cccagcaaga gaatggaag    420 aagcggaccc caaccccata aaggtgggt gttcactctg aataatcctt ccgaagacga    480
gcgcaagaaa atacgggatc ttccaatatc cctatttgat tattttattg ttggcgagga   540
gggtaatgag gaaggacgaa cacctcacct ccagggttc gctaattttg tgaagaagca    600 gactttttaat aaagtgaagt ggtatttggg tgcccgctgc cacatcgaga agcgaaagg    660 aacagatcag cagaataaag aatactgcag taaagaaggc aacttactga tggagtgtgg   720
agctcctaga tctcagggac aacggagtga cctgtctact gctgtgagta ccttgttgga   780
gagcgggagt ctggtgaccg ttgcagagca gcaccctgta acgtttgtca gaaatttccg   840
cgggctggct gaacttttga aagtgagcgg gaaaatgcag aagcgtgatt ggaagactaa   900
tgtacacgtc attgtggggc cacctgggtg tggtaaaagc aaatgggctg ctaattttgc   960
agacccggaa accacatact ggaaaccacc tagaaacaag tggtgggatg gttaccatgg  1020
tgaagaagtg gttgttattg atgacttta tggctggctg ccctgggatg atctactgag  1080
actgtgtgat cgatatccat tgactgtaga gactaaaggt ggaactgtac ctttttttggc  1140 ccgcagtatt ctgattacca gcaatcagac cccgttggaa tggtactcct caactgctgt  1200
cccagctgta gaagctcttt atcggaggat tacttccttg gtattttgga agaatgctac   1260
agaacaatcc acggaggaag ggggccagtt cgtcaccctt ccccccccat gccctgaatt   1320
tccatatgaa ataaattact gagtcttttt tatcacttcg taatggtttt tattattcat   1380
taagggttaa gtgggggtc tttaagatta aattctctga attgtacata catggttaca  1440
cggatattgt attcctggtc gtatatactg ttttcgaacg cagtgccgag gcctacgtgg  1500
tctacatttc cagtagtttg tagtctcagc cacagctgat ttcttttgtt gtttggttgg   1560
aagtaatcaa tagtggaatc taggacaggt ttggggggtaa agtagcggga gtggtaggag   1620
aagggctggg ttatggtatg gcgggaggag tagtttacat aggggtcata ggtgagggct   1680
gtggcctttg ttacaaagtt atcatctaga ataacagcac tggagcccac tcccctgtca  1740
ccctgggtga tcggggagca gggccag                                       1767

<210> SEQ ID NO: 3
<211> LENGTH: 1768
<212> TYPE: DNA
<213> ORGANISM: Porcine circovirus

<400> SEQUENCE: 3
```

-continued

| | |
|---|---|
| aattcaacct taacctttttt tattctgtag tattcaaagg gtatagagat tttgttggtc | 60 |
| ccccctcccg ggggaacaaa gtcgtcaata ttaaatctca tcatgtccac cgcccaggag | 120 |
| ggcgttctga ctgtggtagc cttgacagta tatccgaagg tgcgggagag gcgggtgttg | 180 |
| aagatgccat ttttccttct ccaacggtag cggtggcggg ggtggacgag ccaggggcgg | 240 |
| cggcggagga tctggccaag atggctgcgg ggcggtgtc ttcttctgcg gtaacgcctc | 300 |
| cttggatacg tcatagctga aaacgaaaga agtgcgctgt aagtattacc agcgcacttc | 360 |
| ggcagcggca gcacctcggc agcacctcag cagcaacatg cccagcaaga gaatggaag | 420 |
| aagcggaccc caaccacata aaggtgggt gttcacgctg aataatcctt ccgaagacga | 480 |
| gcgcaagaaa atacgggagc tcccaatctc cctatttgat tattttattg ttggcgagga | 540 |
| gggtaatgag gaaggacgaa cacctcacct ccagggttc gctaattttg tgaagaagca | 600 |
| aactttaat aaagtgaagt ggtatttggg tgcccgctgc cacatcgaga aagccaaagg | 660 |
| aactgatcag cagaataaag aatattgcag taaagaaggc aacttactta ttgaatgtgg | 720 |
| agctcctcga tctcaaggac aacggagtga cctgtctact gctgtgagta ccttgttgga | 780 |
| gagcgggagt ctggtgaccg ttgcagagca gcaccctgta acgtttgtca gaaatttccg | 840 |
| cgggctggct gaacttttga aagtgagcgg gaaaatgcag aagcgtgatt ggaagaccaa | 900 |
| tgtacacgtc attgtgggc cacctggtg tggtaaaagc aaatgggctg ctaattttgc | 960 |
| agacccggaa accacatact ggaaaccacc tagaaacaag tggtgggatg gttaccatgg | 1020 |
| tgaagaagtg gttgttattg atgacttta tggctggctg ccgtgggatg atctactgag | 1080 |
| actgtgtgat cgatatccat tgactgtaga gactaaaggt ggaactgtac cttttttggc | 1140 |
| ccgcagtatt ctgattacca gcaatcagac cccgttggaa tggtactcct caactgctgt | 1200 |
| cccagctgta gaagctctct atcggaggat tacttccttg gtattttgga agaatgctac | 1260 |
| agaacaatcc acgaggaag ggggccagtt cgtcacccttt tccccccat gccctgaatt | 1320 |
| tccatatgaa ataaattact gagtctttttt tatcacttcg taatggtttt tattattcat | 1380 |
| ttagggttta agtgggggggt cttttaagatt aaattctctg aattgtacat acatggttac | 1440 |
| acggatattg tagtcctggt cgtatatact gttttcgaac gcagtgccga ggcctacgtg | 1500 |
| gtccacattt ctagaggttt gtagcctcag ccaaagctga ttcctttttgt tatttggttg | 1560 |
| gaagtaatca atagtggagt caagaacagg tttgggtgtg aagtaacggg agtggtagga | 1620 |
| gaagggttgg gggattgtat ggcgggagga gtagtttaca tatgggtcat aggttagggc | 1680 |
| tgtggccttt gttacaaagt tatcatctag aataacagca gtggagccca ctcccctatc | 1740 |
| accctgggtg atgggggagc agggccag | 1768 |

<210> SEQ ID NO: 4
<211> LENGTH: 1768
<212> TYPE: DNA
<213> ORGANISM: Porcine circovirus

<400> SEQUENCE: 4

| | |
|---|---|
| aattcaacct taacctttct tattctgtag tattcaaagg gtatagagat tttgttggtc | 60 |
| ccccctcccg ggggaacaaa gtcgtcaatt ttaaatctca tcatgtccac cgcccaggag | 120 |
| ggcgttgtga ctgtggtacg cttgacagta tatccgaagg tgcgggagag gcgggtgttg | 180 |
| aagatgccat ttttccttct ccaacggtag cggtggcggg ggtggacgag ccaggggcgg | 240 |
| cggcggagga tctggccaag atggctgcgg ggcggtgtc ttcttctgcg gtaacgcctc | 300 |
| cttggatacg tcatagctga aaacgaaaga agtgcgctgt aagtattacc agcgcacttc | 360 |

-continued

```
ggcagcggca gcacctcggc agcacctcag cagcaacatg cccagcaaga agaatggaag      420
aagcggaccc caaccacata aaaggtgggt gttcacgctg aataatcctt ccgaagacga      480
gcgcaagaaa atacgggagc tcccaatctc cctatttgat tattttattg ttggcgagga      540
gggtaatgag gaaggacgaa cacctcacct ccagggggttc gctaattttg tgaagaagca      600
aacttttaat aaagtgaagt ggtatttggg tgcccgctgc cacatcgaga aagccaaagg      660
aactgatcag cagaataaag aatattgcag taaagaaggc aacttactta ttgaatgtgg      720
agctcctcga tctcaaggac aacggagtga cctgtctact gctgtgagta ccttgttgga      780
gagcgggagt ctggtgaccg ttgcagagca gcaccctgta acgtttgtca gaaatttccg      840
cgggctggct gaacttttga aagtgagcgg aaaatgcag aagcgtgatt ggaagaccaa      900
tgtacacgtc attgtggggc cacctgggtg tggtaaaagc aaatgggctg ctaattttgc      960
agacccggaa accacatact ggaaaccacc tagaaacaag tggtgggatg gttaccatgg     1020
tgaagaagtg gttgttattg atgactttta tggctggctg ccgtgggatg atctactgag     1080
actgtgtgat cgatatccat tgactgtaga gactaaaggt ggaactgtac cttttttggc     1140
ccgcagtatt ctgattacca gcaatcagac cccgttggaa tggtactcct caactgctgt     1200
cccagctgta gaagctctct atcggaggat tacttccttg gtattttgga gaatgctac     1260 agaacaatcc acggaggaag ggggccagtt cgtcacccct tcccccccat gccctgaatt     1320
tccatatgaa ataaattact gagtcttttt tatcacttcg taatggtttt tattattcat     1380
ttagggttta agtgggggt ctttaagatt aaattctctg aattgtacat acatggttac     1440
acggatattg tagtcctggt cgtatttact gttttcgaac gcagcgccga ggcctacgtg     1500
gtccacattt ccagaggttt gtagtctcag ccaaagctga ttccttttgt tatttggttg     1560
gaagtaatca atagtggagt caagaacagg tttgggtgtg aagtaacggg agtggtagga     1620
gaagggttgg gggattgtat ggcgggagga gtagtttaca tatgggtcat aggttagggc     1680
tgtggccttt gttacaaagt tatcatctag aataacagca gtggagccca ctcccctatc     1740
accctgggtg atgggggagc agggccag                                          1768
```

<210> SEQ ID NO: 5
<211> LENGTH: 1759
<212> TYPE: DNA
<213> ORGANISM: Porcine circovirus

<400> SEQUENCE: 5

```
aattcatatt tagcctttct aatacggtag tattggaaag gtagggggtag ggggttggtg       60 ccgcctgagg gggggaggaa ctggccgatg ttgaatttga ggtagttaac attccaagat      120
ggctgcgagt atcctccttt tatggtgagt acaaattctg tagaaaggcg ggaattgaag      180 ataccgtct ttcggcgcca tctgtaacgg tttctgaagg cggggtgtgc caaatatggt      240
cttctccgga ggatgtttcc aagatggctg cggggcggg tccttcttct gcggtaacgc      300
ctccttggcc acgtcatcct ataaaagtga agaagtgcg ctgctgtagt attaccagcg      360
cacttcggca gcggcagcac ctcggcagcg tcagtgaaaa tgccaagcaa gaaaagcggc      420
ccgcaacccc ataagaggtg ggtgttcacc cttaataatc cttccgagga ggagaaaaac      480
aaaatacggg agcttccaat ctccctttttt gattattttg tttgcggaga ggaaggtttg      540
gaagagggta gaactcctca cctccagggg tttgcgaatt ttgctaagaa gcagactttt      600
aacaaggtga agtggtattt ggtgcccgc tgccacatcg agaaagcgaa aggaaccgac      660
```

```
cagcagaata aagaatactg cagtaaagaa ggccacatac ttatcgagtg tggagctccg    720
cggaaccagg ggaagcgcag cgacctgtct actgctgtga gtaccctttt ggagacgggg    780
tctttggtga ctgtagccga gcagttccct gtaacgtatg tgagaaattt ccgcgggctg    840
gctgaacttt tgaaagtgag cgggaagatg cagcagcgtg attggaagac agctgtacac    900
gtcatagtgg gcccgcccgg ttgtgggaag agccagtggg cccgtaattt tgctgagcct    960
agggacacct actggaagcc tagtagaaat aagtggtggg atggatatca tggagaagaa   1020
gttgttgttt tggatgattt ttatggctgg ttaccttggg atgatctact gagactgtgt   1080
gaccggtatc cattgactgt agagactaaa ggggtactg ttccttttt ggcccgcagt    1140 attttgatta ccagcaatca ggcccccag gaatggtact cctcaactgc tgtcccagct    1200
gtagaagctc tctatcggag gattactact ttgcaatttt ggaagactgc tggagaacaa   1260
tccacggagg tacccgaagg ccgatttgaa gcagtggacc caccctgtgc cctttccca    1320 tataaaataa attactgagt cttttttgtt atcacatcgt aatggttttt atttttattt   1380
atttagaggg tcttttagga taaattctct gaattgtaca taaatagtca gccttaccac   1440
ataattttgg gctgtggctg cattttggag cgcatagccg aggcctgtgt gctcgacatt   1500
ggtgtgggta tttaaatgga gccacagctg gtttctttta ttatttgggt ggaaccaatc   1560
aattgtttgg tccagctcag gtttgggggt gaagtacctg gagtggtagg taaagggctg   1620
ccttatggtg tggcgggagg agtagttaat ataggggtca taggccaagt tggtggaggg   1680
ggttacaaag ttggcatcca agataacaac agtggaccca cacctcttt gattagaggt   1740 gatggggtct ctggggtaa                                                1759
```